(12) United States Patent
Jahng

(10) Patent No.: US 7,763,052 B2
(45) Date of Patent: Jul. 27, 2010

(54) METHOD AND APPARATUS FOR FLEXIBLE FIXATION OF A SPINE

(75) Inventor: Tae-ahn Jahng, Iksan (KR)

(73) Assignee: N Spine, Inc., San Diego, CA (US)

( * ) Notice: Subject to any disclaimer, the term of this patent is extended or adjusted under 35 U.S.C. 154(b) by 383 days.

(21) Appl. No.: 10/798,014

(22) Filed: Mar. 10, 2004

(65) Prior Publication Data

US 2005/0124991 A1   Jun. 9, 2005

Related U.S. Application Data

(63) Continuation-in-part of application No. 10/728,566, filed on Dec. 5, 2003.

(51) Int. Cl.
*A61B 17/70* (2006.01)
(52) U.S. Cl. .................. 606/254; 403/220
(58) Field of Classification Search .......... 606/61; 403/220, 223, 229, 291
See application file for complete search history.

(56) References Cited

U.S. PATENT DOCUMENTS

| | | | |
|---|---|---|---|
| 2,379,577 A | 7/1945 | Harsted | |
| 3,635,233 A | 1/1972 | Robertson | |
| 3,669,133 A | 6/1972 | Hyman | |
| 4,041,939 A | 8/1977 | Hall | |
| 4,369,769 A | 1/1983 | Edwards | |
| 4,378,712 A * | 4/1983 | Yoshifuji | 74/502.5 |
| 4,448,191 A | 5/1984 | Rodnyansky et al. | |
| 4,483,562 A | 11/1984 | Schoolman | |
| 4,743,260 A | 5/1988 | Burton | |
| 4,932,975 A | 6/1990 | Main et al. | |
| 4,960,410 A * | 10/1990 | Pinchuk | 604/96.01 |
| 4,979,531 A | 12/1990 | Toor et al. | |
| 5,002,576 A | 3/1991 | Fuhrmann et al. | |
| 5,011,497 A | 4/1991 | Persson et al. | |
| 5,029,847 A | 7/1991 | Ross | |
| 5,030,220 A | 7/1991 | Howland | |
| 5,055,104 A | 10/1991 | Ray | |

(Continued)

FOREIGN PATENT DOCUMENTS

DE   2821678   11/1979

(Continued)

OTHER PUBLICATIONS

International Search Report for PCT/US04/30732, mailed on Oct. 14, 2005, 2 pages.

(Continued)

*Primary Examiner*—Eduardo C Robert
*Assistant Examiner*—Mary Hoffman
(74) *Attorney, Agent, or Firm*—Stroock, Stroock & Lavan LLP

(57) ABSTRACT

A flexible spinal fixation device having a flexible metallic connection unit for non-rigid stabilization of the spinal column. In one embodiment, the fixation device includes at least two securing members configured to be inserted into respective adjacent spinal pedicles, each securing member each including a coupling assembly. The fixation device further includes a flexible metal connection unit configured to be received and secured within the coupling assemblies of each securing member so as to flexibly stabilize the affected area of the spine.

20 Claims, 26 Drawing Sheets

U.S. PATENT DOCUMENTS

| | | | |
|---|---|---|---|
| 5,084,048 A | 1/1992 | Jacob et al. | |
| 5,092,867 A | 3/1992 | Harms et al. | |
| 5,133,716 A | 7/1992 | Plaza | |
| 5,180,393 A * | 1/1993 | Commarmond | 623/13.14 |
| 5,246,442 A | 9/1993 | Ashman et al. | |
| 5,251,611 A | 10/1993 | Zehel et al. | |
| 5,282,863 A | 2/1994 | Burton | |
| 5,375,823 A | 12/1994 | Navas | |
| 5,387,213 A | 2/1995 | Breard et al. | |
| 5,413,576 A | 5/1995 | Rivard | |
| 5,415,661 A | 5/1995 | Holmes | |
| 5,423,816 A | 6/1995 | Lin | |
| 5,480,401 A | 1/1996 | Navas | |
| 5,488,761 A * | 2/1996 | Leone | 29/2.25 |
| 5,536,268 A | 7/1996 | Griss | |
| 5,540,688 A | 7/1996 | Navas | |
| 5,562,737 A | 10/1996 | Graf | |
| 5,573,520 A * | 11/1996 | Schwartz et al. | 604/526 |
| 5,649,925 A | 7/1997 | Barbera Alacreu | |
| 5,658,286 A | 8/1997 | Sava | |
| 5,662,651 A | 9/1997 | Tornier et al. | |
| 5,672,175 A * | 9/1997 | Martin | 606/86 A |
| 5,681,311 A | 10/1997 | Foley et al. | |
| 5,688,275 A | 11/1997 | Koros et al. | |
| 5,713,900 A | 2/1998 | Benzel et al. | |
| 5,725,582 A | 3/1998 | Bevan et al. | |
| 5,733,284 A | 3/1998 | Martin | |
| 5,814,046 A | 9/1998 | Hopf | |
| RE36,221 E | 6/1999 | Breard et al. | |
| 5,964,767 A * | 10/1999 | Tapia et al. | 606/73 |
| 6,053,922 A | 4/2000 | Krause et al. | |
| 6,187,000 B1 | 2/2001 | Davison et al. | |
| 6,193,720 B1 | 2/2001 | Yuan et al. | |
| 6,241,730 B1 | 6/2001 | Alby | |
| 6,267,764 B1 | 7/2001 | Elberg | |
| 6,290,700 B1 | 9/2001 | Schmotzer | |
| 6,293,949 B1 | 9/2001 | Justis et al. | |
| 6,296,644 B1 | 10/2001 | Saurat et al. | |
| 6,337,142 B2 | 1/2002 | Harder et al. | |
| 6,402,750 B1 | 6/2002 | Atkinson et al. | |
| 6,440,169 B1 | 8/2002 | Elberg et al. | |
| 6,447,518 B1 | 9/2002 | Krause et al. | |
| 6,447,546 B1 * | 9/2002 | Bramlet et al. | 623/17.16 |
| 6,475,220 B1 | 11/2002 | Whiteside | |
| 6,475,242 B1 * | 11/2002 | Bramlet | 623/21.11 |
| 6,488,682 B2 | 12/2002 | Kikuchi et al. | |
| 6,530,934 B1 | 3/2003 | Jacobsen et al. | |
| 6,554,831 B1 | 4/2003 | Rivard et al. | |
| 6,576,018 B1 | 6/2003 | Holt | |
| 6,585,769 B1 | 7/2003 | Muhanna et al. | |
| 6,589,246 B1 | 7/2003 | Hack et al. | |
| 6,626,905 B1 | 9/2003 | Schmiel et al. | |
| 6,626,909 B2 | 9/2003 | Chin | |
| 6,645,207 B2 | 11/2003 | Dixon et al. | |
| 6,652,585 B2 | 11/2003 | Lange | |
| 6,682,533 B1 | 1/2004 | Dinsdale et al. | |
| 6,706,044 B2 | 3/2004 | Kuslich et al. | |
| 6,749,614 B2 | 6/2004 | Teitelbaum et al. | |
| 6,783,527 B2 | 8/2004 | Drewry et al. | |
| 6,827,743 B2 | 12/2004 | Eisermann et al. | |
| 6,835,205 B2 | 12/2004 | Atkinson et al. | |
| 6,884,241 B2 | 4/2005 | Bertranou et al. | |
| 6,966,910 B2 | 11/2005 | Ritland | |
| 6,986,771 B2 * | 1/2006 | Paul et al. | 606/61 |
| 6,989,011 B2 | 1/2006 | Paul et al. | |
| 7,083,621 B2 | 8/2006 | Shaolian et al. | |
| 7,094,237 B2 | 8/2006 | Gradel et al. | |
| 7,097,648 B1 * | 8/2006 | Globerman et al. | 606/99 |
| 7,125,410 B2 | 10/2006 | Freudiger | |
| 7,229,441 B2 | 6/2007 | Trieu et al. | |
| 7,335,200 B2 | 2/2008 | Carli | |
| 7,556,639 B2 | 7/2009 | Rothman et al. | 606/257 |
| 2001/0020169 A1 | 9/2001 | Metz-Stavenhagen | |
| 2001/0037111 A1 | 11/2001 | Dixon et al. | |
| 2001/0049559 A1 * | 12/2001 | Koo et al. | 623/17.16 |
| 2002/0010467 A1 | 1/2002 | Cooper et al. | |
| 2002/0035366 A1 | 3/2002 | Walder et al. | |
| 2002/0049394 A1 | 4/2002 | Roy et al. | |
| 2002/0055740 A1 | 5/2002 | Lieberman | |
| 2002/0065557 A1 | 5/2002 | Goble et al. | |
| 2002/0082600 A1 | 6/2002 | Shaolian et al. | |
| 2002/0087159 A1 | 7/2002 | Thomas | |
| 2002/0095154 A1 | 7/2002 | Atkinson et al. | |
| 2002/0099378 A1 | 7/2002 | Michelson | |
| 2002/0107570 A1 | 8/2002 | Sybert et al. | |
| 2002/0111628 A1 | 8/2002 | Ralph et al. | |
| 2002/0111630 A1 | 8/2002 | Ralph et al. | |
| 2002/0120270 A1 | 8/2002 | Trieu et al. | |
| 2002/0123668 A1 | 9/2002 | Ritland | |
| 2002/0123750 A1 | 9/2002 | Eisermann et al. | |
| 2002/0123806 A1 | 9/2002 | Reiley | |
| 2002/0138077 A1 | 9/2002 | Ferree | |
| 2002/0143329 A1 | 10/2002 | Serhan et al. | |
| 2002/0143401 A1 | 10/2002 | Michelson | |
| 2002/0169450 A1 | 11/2002 | Lange | |
| 2002/0183748 A1 | 12/2002 | Martin et al. | |
| 2002/0198526 A1 | 12/2002 | Shaolian et al. | |
| 2003/0032958 A1 | 2/2003 | Soubeiran | |
| 2003/0040746 A1 | 2/2003 | Mitchell et al. | |
| 2003/0040797 A1 | 2/2003 | Fallin et al. | |
| 2003/0045875 A1 | 3/2003 | Bertranou et al. | |
| 2003/0055426 A1 | 3/2003 | Carbone et al. | |
| 2003/0060823 A1 | 3/2003 | Bryan | |
| 2003/0073998 A1 | 4/2003 | Pagliuca et al. | |
| 2003/0083657 A1 | 5/2003 | Drewry et al. | |
| 2003/0083688 A1 | 5/2003 | Simonson | |
| 2003/0088251 A1 | 5/2003 | Braun et al. | |
| 2003/0093078 A1 | 5/2003 | Ritland | |
| 2003/0109880 A1 * | 6/2003 | Shirado et al. | 606/61 |
| 2003/0171749 A1 | 9/2003 | Le Couedic et al. | |
| 2003/0191371 A1 | 10/2003 | Smith et al. | |
| 2003/0191470 A1 | 10/2003 | Ritland | |
| 2003/0195514 A1 | 10/2003 | Trieu et al. | |
| 2003/0195551 A1 | 10/2003 | Davison et al. | |
| 2003/0220643 A1 * | 11/2003 | Ferree | 606/61 |
| 2004/0002708 A1 | 1/2004 | Ritland | |
| 2004/0049189 A1 | 3/2004 | Le Couedic et al. | |
| 2004/0049190 A1 | 3/2004 | Biedermann et al. | |
| 2004/0138661 A1 | 7/2004 | Bailey | |
| 2004/0143264 A1 | 7/2004 | McAfee | |
| 2004/0147928 A1 | 7/2004 | Landry et al. | |
| 2004/0172025 A1 | 9/2004 | Drewry et al. | |
| 2004/0215191 A1 | 10/2004 | Kitchen | |
| 2004/0215193 A1 | 10/2004 | Shaolian et al. | |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2004/0267260 A1 | 12/2004 | Mack et al. | |
| 2005/0033295 A1 | 2/2005 | Wisnewski | |
| 2005/0033299 A1 | 2/2005 | Shluzas | |
| 2005/0038432 A1 | 2/2005 | Shaolian et al. | |
| 2005/0049708 A1 | 3/2005 | Atkinson et al. | |
| 2005/0065516 A1 | 3/2005 | Jahng | |
| 2005/0085815 A1 | 4/2005 | Harms et al. | |
| 2005/0090822 A1 | 4/2005 | DiPoto | |
| 2005/0101957 A1 | 5/2005 | Buskirk et al. | |
| 2005/0113927 A1 | 5/2005 | Malek | |
| 2005/0131407 A1 | 6/2005 | Sicvol et al. | 606/61 |
| 2005/0154390 A1 | 7/2005 | Biedermann et al. | |
| 2005/0165396 A1 | 7/2005 | Fortin et al. | |
| 2005/0171539 A1 | 8/2005 | Braun et al. | |
| 2005/0171540 A1 | 8/2005 | Lim et al. | |
| 2005/0171543 A1 | 8/2005 | Timm et al. | |
| 2005/0177156 A1 | 8/2005 | Timm et al. | |

| | | | | | | |
|---|---|---|---|---|---|---|
| 2005/0177157 A1 | 8/2005 | Jahng | | 2007/0149909 A1 | 6/2007 | Fortin et al. |
| 2005/0182401 A1 | 8/2005 | Timm et al. | | 2007/0198088 A1 | 8/2007 | Biedermann et al. |
| 2005/0182409 A1 | 8/2005 | Callahan et al. | | 2008/0195149 A1 | 8/2008 | Burke |
| 2005/0203511 A1 | 9/2005 | Wilson-MacDonald et al. | | | | |
| 2005/0203513 A1 | 9/2005 | Jahng et al. | | | | |
| 2005/0203517 A1 | 9/2005 | Jahng et al. | | | | |
| 2005/0203519 A1 | 9/2005 | Harms et al. | | | | |
| 2005/0222569 A1 | 10/2005 | Panjabi | | | | |
| 2005/0228381 A1 | 10/2005 | Kirschman | | | | |
| 2005/0245930 A1 | 11/2005 | Timm et al. | | | | |
| 2005/0261682 A1 | 11/2005 | Ferree | | | | |
| 2005/0261685 A1 | 11/2005 | Fortin et al. | | | | |
| 2005/0261686 A1 | 11/2005 | Paul | | | | |
| 2005/0277922 A1 | 12/2005 | Trieu et al. | | | | |
| 2005/0288670 A1 | 12/2005 | Panjabi et al. | | | | |
| 2005/0288672 A1 | 12/2005 | Ferree .................. 606/61 | | | | |
| 2006/0015100 A1 | 1/2006 | Panjabi et al. | | | | |
| 2006/0036240 A1 | 2/2006 | Colleran et al. | | | | |
| 2006/0084982 A1 | 4/2006 | Kim | | | | |
| 2006/0111715 A1 | 5/2006 | Jackson | | | | |
| 2006/0129147 A1 | 6/2006 | Biedermann et al. | | | | |
| 2006/0142758 A1 | 6/2006 | Petit | | | | |
| 2006/0142760 A1 | 6/2006 | McDonnell | | | | |
| 2006/0149238 A1 | 7/2006 | Sherman et al. | | | | |
| 2006/0189983 A1 | 8/2006 | Fallin et al. | | | | |
| 2006/0189984 A1 | 8/2006 | Fallin et al. | | | | |
| 2006/0212033 A1 | 9/2006 | Rothman et al. | | | | |
| 2006/0229612 A1 | 10/2006 | Rothman et al. | | | | |
| 2006/0240533 A1 | 10/2006 | Sengupta et al. | | | | |
| 2006/0260483 A1 | 11/2006 | Hartmann et al. | | | | |
| 2006/0264940 A1 | 11/2006 | Hartmann | | | | |
| 2006/0293657 A1 | 12/2006 | Hartmann | | | | |
| 2007/0016193 A1 | 1/2007 | Ritland | | | | |
| 2007/0073293 A1 | 3/2007 | Martz et al. | | | | |
| 2007/0123865 A1 | 5/2007 | Schlapfer et al. | | | | |
| 2007/0129729 A1 | 6/2007 | Petit et al. | | | | |

FOREIGN PATENT DOCUMENTS

| | | |
|---|---|---|
| DE | 4109941 | 10/1992 |
| DE | 4239716 | 8/1994 |
| EP | 0677277 | 3/1995 |
| EP | 0669109 | 8/1995 |
| FR | 2702363 | 3/1993 |
| FR | 2717370 | 9/1995 |
| FR | 2718946 | 10/1995 |
| FR | 2799949 | 4/2001 |
| GB | 2382304 | 5/2003 |
| JP | 2002224131 | 8/2002 |
| WO | WO 2005/039454 | 5/2005 |
| WO | WO 2005/044117 | 5/2005 |
| WO | WO 2005/092222 | 10/2005 |
| WO | WO 2005/094704 | 10/2005 |
| WO | WO 2005/110257 | 11/2005 |

OTHER PUBLICATIONS

Kanayama et al., Journal of Neurosurgery (2001) 95(Spine 1):5-10.
Markwalder and Wenger, Acta Neurochirurgica (2003) 145(3):209-214.
Mulholland and Sengupta, European Spine Journal (2002) 11 (Suppl 2):S198-205.
Schmoelz et al., Journal of Spinal Disorders & Techniques (2003) 16(4):418-423.
Stoll et al., European Spine Journal (2002) 11 (Suppl 2):S170-178.
International Search Report for PCT/US05/46659, mailed on Aug. 14, 2006, 3 pages.
International Search Report for PCT/US05/44372, mailed on Sep. 20, 2006, 3 pages.

* cited by examiner

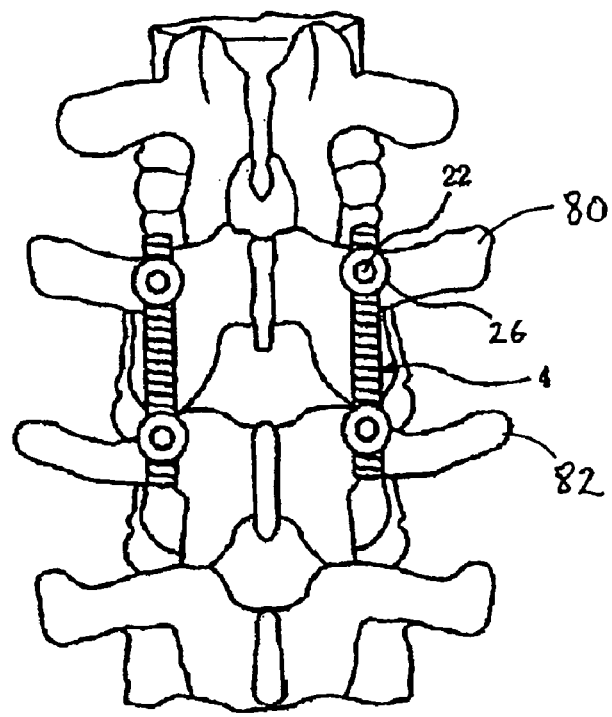
FIGURE 21
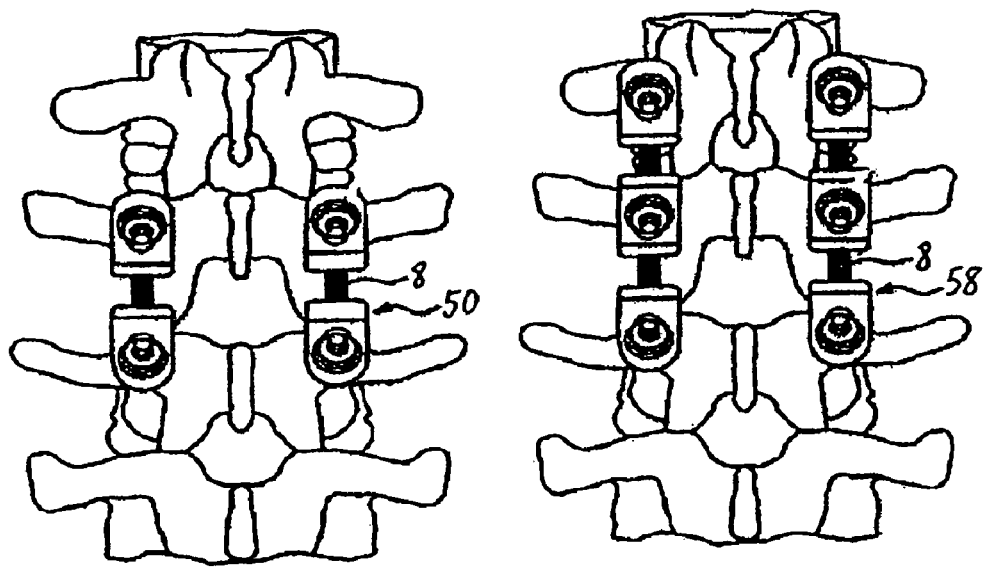
FIGURE 22A
FIGURE 22B

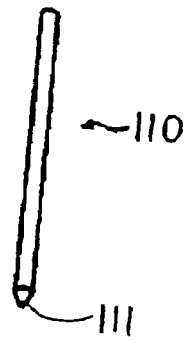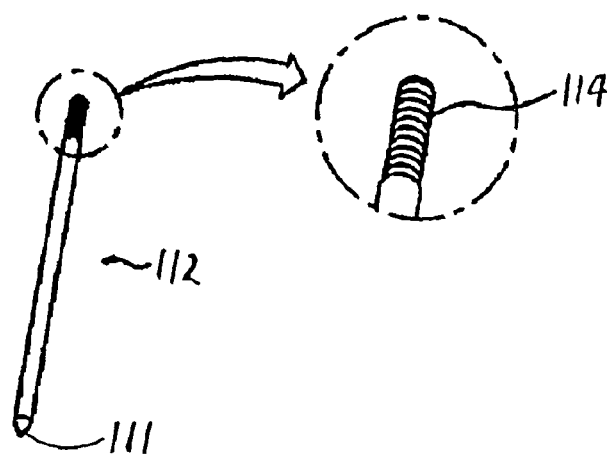
FIGURE 27A  FIGURE 27B
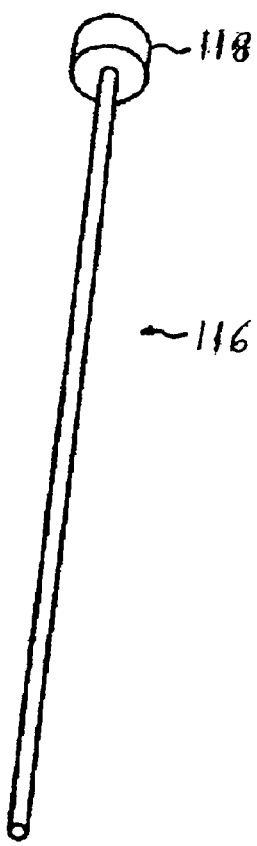
FIGURE 28

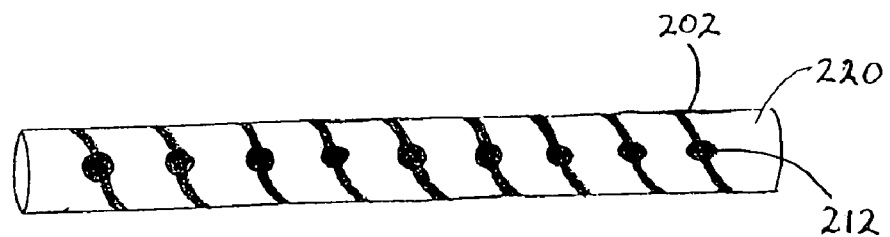
FIGURE 38B
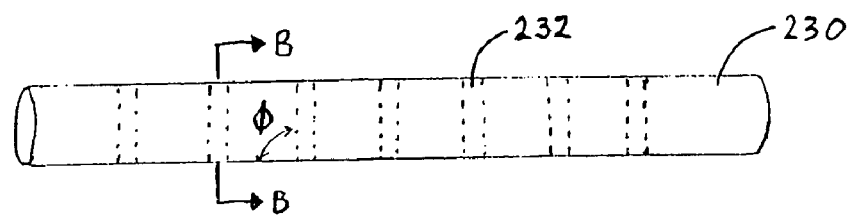
FIGURE 39A
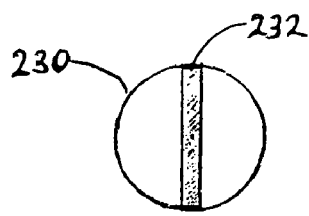 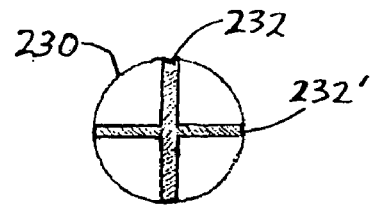
FIGURE 39B  FIGURE 39C

METHOD AND APPARATUS FOR FLEXIBLE FIXATION OF A SPINE

CROSS-REFERENCE TO RELATED APPLICATIONS

The present application is a continuation-in-part of U.S. patent application Ser. No. 10/728,566, filed Dec. 5, 2003, entitled "A Method and Apparatus for Flexible Fixation of a Spine."

BACKGROUND OF THE INVENTION

1. Field of the Invention

The present invention relates to a method and system for fixing and stabilizing a spinal column and, more particularly, to a method and system of spinal fixation in which one or more screw type fixing members are implanted and fixed into a portion of a patient's spinal column and flexible, semi-rigid rods or plates are connected and fixed to the upper ends of the fixing members to provide dynamic stabilization of the spinal column.

2. Description of the Related Art

Degenerative spinal column diseases, such as disc degenerative diseases (DDD), spinal stenosis, spondylolisthesis, and so on, need surgical operation if they do not take a turn for the better by conservative management. Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Conventional methods of spinal fixation utilize a rigid spinal fixation device to support an injured spinal part and prevent movement of the injured part. These conventional spinal fixation devices include: fixing screws configured to be inserted into the spinal pedicle or sacral of the backbone to a predetermined depth and angle, rods or plates configured to be positioned adjacent to the injured spinal part, and coupling elements for connecting and coupling the rods or plates to the fixing screws such that the injured spinal part is supported and held in a relatively fixed position by the rods or plates.

U.S. Pat. No. 6,193,720 discloses a conventional spinal fixation device, in which connection members of a rod or plate type are mounted on the upper ends of at least one or more screws inserted into the spinal pedicle or sacral of the backbone. The connection units, such as the rods and plates, are used to stabilize the injured part of the spinal column which has been weakened by decompression. The connection units also prevent further pain and injury to the patient by substantially restraining the movement of the spinal column. However, because the connection units prevent normal movement of the spinal column, after prolonged use, the spinal fixation device can cause ill effects, such as "junctional syndrome" (transitional syndrome) or "fusion disease" resulting in further complications and abnormalities associated with the spinal column. In particular, due to the high rigidity of the rods or plates used in conventional fixation devices, the patient's fixed joints are not allowed to move after the surgical operation, and the movement of the spinal joints located above or under the operated area is increased. Consequently, such spinal fixation devices cause decreased mobility of the patient and increased stress and instability to the spinal column joints adjacent to the operated area.

It has been reported that excessive rigid spinal fixation is not helpful to the fusion process due to load shielding caused by rigid fixation. Thus, trials using load sharing semi-rigid spinal fixation devices have been performed to eliminate this problem and assist the bone fusion process. For example, U.S. Pat. No. 5,672,175, U.S. Pat. No. 5,540,688, and U.S. Pub No. 2001/0037111 disclose dynamic spine stabilization devices having flexible designs that permit axial load translation (i.e., along the vertical axis of the spine) for bone fusion promotion. However, because these devices are intended for use following a bone fusion procedure, they are not well-suited for spinal fixation without fusion. Thus, in the end result, these devices do not prevent the problem of rigid fixation resulting from fusion.

To solve the above-described problems associated with rigid fixation, non-fusion technologies have been developed. The Graf band is one example of a non-fusion fixation device that is applied after decompression without bone fusion. The Graf band is composed of a polyethylene band and pedicle screws to couple the polyethylene band to the spinal vertebrae requiring stabilization. The primary purpose of the Graf band is to prevent sagittal rotation (flexion instability) of the injured spinal parts. Thus, it is effective in selected cases but is not appropriate for cases that require greater stability and fixation. See, Kanayama et al, Journal of Neurosurgery 95(1 Suppl):5-10, 2001, Markwalder & Wenger, Acta Neurochrgica 145(3):209-14.). Another non-fusion fixation device called "Dynesys" has recently been introduced. See Stoll et al, European Spine Journal 11 Suppl 2:S170-8, 2002, Schmoelz et al, J of spinal disorder & techniques 16(4):418-23, 2003. The Dynesys device is similar to the Graf band except it uses a polycarburethane spacer between the screws to maintain the distance between the heads of two corresponding pedicle screws and, hence, adjacent vertebrae in which the screws are fixed. Early reports by the inventors of the Dynesys device indicate it has been successful in many cases. However, it has not yet been determined whether the Dynesys device can maintain long-term stability with flexibility and durability in a controlled study. Because it has polyethylene components and interfaces, there is a risk of mechanical failure. Furthermore, due to the mechanical configuration of the device, the surgical technique required to attach the device to the spinal column is complex and complicated.

U.S. Pat. Nos. 5,282,863 and 4,748,260 disclose a flexible spinal stabilization system and method using a plastic, non-metallic rod. U.S. patent publication No. 2003/0083657 discloses another example of a flexible spinal stabilization device that uses a flexible elongate member. These devices are flexible but they are not well-suited for enduring long-term axial loading and stress. Additionally, the degree of desired flexibility vs. rigidity may vary from patient to patient. The design of existing flexible fixation devices are not well suited to provide varying levels of flexibility to provide optimum results for each individual candidate. For example, U.S. Pat.

No. 5,672,175 discloses a flexible spinal fixation device which utilizes a flexible rod made of metal alloy and/or a composite material. Additionally, compression or extension springs are coiled around the rod for the purpose of providing de-rotation forces on the vertebrae in a desired direction. However, this patent is primarily concerned with providing a spinal fixation device that permits "relative longitudinal translational sliding movement along [the] vertical axis" of the spine and neither teaches nor suggests any particular designs of connection units (e.g., rods or plates) that can provide various flexibility characteristics. Prior flexible rods such as that mentioned in U.S. Pat. No. 5,672,175 typically have solid construction with a relatively small diameter in order to provide a desired level of flexibility. Because they are typically very thin to provide suitable flexibility, such prior art rods are prone to mechanical failure and have been known to break after implantation in patients.

Therefore, conventional spinal fixation devices have not provided a comprehensive and balanced solution to the problems associated with curing spinal diseases. Many of the prior devices are characterized by excessive rigidity, which leads to the problems discussed above while others, though providing some flexibility, are not well-adapted to provide varying degrees of flexibility. Additionally, existing flexible fixation devices utilize non-metallic components that are not proven to provide long-term stability and durability. Therefore, there is a need for an improved dynamic spinal fixation device that provides a desired level of flexibility to the injured parts of the spinal column, while also providing long-term durability and consistent stabilization of the spinal column.

Additionally, in a conventional surgical method for fixing the spinal fixation device to the spinal column, a doctor incises the midline of the back to about 10-15 centimeters, and then, dissects and retracts it to both sides. In this way, the doctor performs muscular dissection to expose the outer part of the facet joint. Next, after the dissection, the doctor finds an entrance point to the spinal pedicle using radiographic devices (e.g., C-arm flouroscopy), and inserts securing members of the spinal fixation device (referred to as "spinal pedicle screws") into the spinal pedicle. Thereafter, the connection units (e.g., rods or plates) are attached to the upper portions of the pedicle screws in order to provide support and stability to the injured portion of the spinal column. Thus, in conventional spinal fixation procedures, the patient's back is incised about 10~15 cm, and as a result, the back muscle, which is important for maintaining the spinal column, is incised or injured, resulting in significant post-operative pain to the patient and a slow recovery period.

Recently, to reduce patient trauma, a minimally invasive surgical procedure has been developed which is capable of performing spinal fixation surgery through a relatively small hole or "window" that is created in the patient's back at the location of the surgical procedure. Through the use of an endoscope, or microscope, minimally invasive surgery allows a much smaller incision of the patient's affected area. Through this smaller incision, two or more securing members (e.g., pedicle screws) of the spinal fixation device are screwed into respective spinal pedicle areas using a navigation system. Thereafter, special tools are used to connect the stabilizing members (e.g., rods or plates) of the fixation device to the securing members. Alternatively, or additionally, the surgical procedure may include inserting a step dilator into the incision and then gradually increasing the diameter of the dilator. Thereafter, a tubular retractor is inserted into the dilated area to retract the patient's muscle and provide a visual field for surgery. After establishing this visual field, decompression and, if desired, fusion procedures may be performed, followed by a fixation procedure, which includes the steps of finding the position of the spinal pedicle, inserting pedicle screws into the spinal pedicle, using an endoscope or a microscope, and securing the stabilization members (e.g., rods or plates) to the pedicle screws in order to stabilize and support the weakened spinal column.

One of the most challenging aspects of performing the minimally invasive spinal fixation procedure is locating the entry point for the pedicle screw under endoscopic or microscopic visualization. Usually anatomical landmarks and/or radiographic devices are used to find the entry point, but clear anatomical relationships are often difficult to identify due to the confined working space. Additionally, the minimally invasive procedure requires that a significant amount of the soft tissue must be removed to reveal the anatomy of the regions for pedicle screw insertion. The removal of this soft tissue results in bleeding in the affected area, thereby adding to the difficulty of finding the correct position to insert the securing members and causing damage to the muscles and soft tissue surrounding the surgical area. Furthermore, because it is difficult to accurately locate the point of insertion for the securing members, conventional procedures are unnecessarily traumatic.

Radiography techniques have been proposed and implemented in an attempt to more accurately and quickly find the position of the spinal pedicle in which the securing members will be inserted. However, it is often difficult to obtain clear images required for finding the corresponding position of the spinal pedicle using radiography techniques due to radiographic interference caused by metallic tools and equipment used during the surgical operation. Moreover, reading and interpreting radiographic images is a complex task requiring significant training and expertise. Radiography poses a further problem in that the patient is exposed to significant amounts of radiation.

Although some guidance systems have been developed which guide the insertion of a pedicle screw to the desired entry point on the spinal pedicle, these prior systems have proven difficult to use and, furthermore, hinder the operation procedure. For example, prior guidance systems for pedicle screw insertion utilize a long wire that is inserted through a guide tube that is inserted through a patient's back muscle and tissue. The location of insertion of the guide tube is determined by radiographic means (e.g., C-arm flouroscope) and driven until a first end of the guide tube reaches the desired location on the surface of the pedicle bone. Thereafter, a first end of the guide wire, typically made of a biocompatible metal material, is inserted into the guide tube and pushed into the pedicle bone, while the opposite end of the wire remains protruding out of the patient's back. After the guide wire has been fixed into the pedicle bone, the guide tube is removed, and a hole centered around the guide wire is dilated and retracted. Finally, a pedicle screw having an axial hole or channel configured to receive the guide wire therethrough is guided by the guide wire to the desired location on the pedicle bone, where the pedicle screw is screw-driven into the pedicle.

Although the concept of the wire guidance system is a good one, in practice, the guide wire has been very difficult to use. Because it is a relatively long and thin wire, the structural integrity of the guide wire often fails during attempts to drive one end of the wire into the pedicle bone, making the process unnecessarily time-consuming and laborious. Furthermore, because the wire bends and crimps during insertion, it does not provide a smooth and secure anchor for guiding subsequent tooling and pedicle screws to the entry point on the pedicle. Furthermore, current percutaneous wire guiding systems are used in conjunction with C-arm flouroscopy (or other radiographic device) without direct visualization with the use of an endoscope or microscope. Thus, current wire guidance systems pose a potential risk of misplacement or pedicle breakage. Finally, because one end of the wire remains protruding out of the head of the pedicle screw, and the patient's back, this wire hinders freedom of motion by the surgeon in performing the various subsequent procedures involved in spinal fixation surgery. Thus, there is a need to provide an improved guidance system, adaptable for use in minimally invasive pedicle screw fixation procedures under endoscopic or microscopic visualization, which is easier to implant into the spinal pedicle and will not hinder subsequent procedures performed by the surgeon.

As discussed above, existing methods and devices used to cure spinal diseases are in need of much improvement. Most conventional spinal fixation devices are too rigid and inflexible. This excessive rigidity causes further abnormalities and diseases of the spine, as well as significant discomfort to the patient. Although some existing spinal fixation devices do provide some level of flexibility, these devices are not designed or manufactured so that varying levels of flexibility may be easily obtained to provide a desired level of flexibility for each particular patient. Additionally, prior art devices having flexible connection units (e.g., rods or plates) pose a greater risk of mechanical failure and do not provide long-term durability and stabilization of the spine. Furthermore, existing methods of performing the spinal fixation procedure are unnecessarily traumatic to the patient due to the difficulty in finding the precise location of the spinal pedicle or sacral of the backbone where the spinal fixation device will be secured.

BRIEF SUMMARY OF THE INVENTION

The invention addresses the above and other needs by providing an improved method and system for stabilizing an injured or weakened spinal column.

To overcome the deficiencies of conventional spinal fixation devices, in one embodiment, the inventor of the present invention has invented a novel flexible spinal fixation device with an improved construction and design that uses metal or metal-synthetic hybrid components to provide a desired level of flexibility, stability and durability.

As a result of long-term studies to reduce the operation time required for minimally invasive spinal surgery, to minimize injury to tissues near the surgical area, in another embodiment, the invention provides a method and device for accurately and quickly finding a position of the spinal column in which securing members of the spinal fixation device will be inserted. A novel guidance/marking device is used to indicate the position in the spinal column where the securing members will be inserted.

BRIEF DESCRIPTION OF THE DRAWINGS

FIG. 21 illustrates a perspective view of the spinal fixation device of FIG. 1 after it has been implanted into a patient's spinal column.

FIGS. 22A and 22B provide perspective views of spinal fixation devices utilizing the plate connection units of FIGS. 16A and 16B, respectively.

FIGS. 27A and 27B illustrate perspective views of two embodiments of a fiducial pin, respectively.

FIG. 28 is a perspective view of a pushing trocar in accordance with a further embodiment of the invention.

FIG. 38B is a top view of the flexible rod of FIG. 38A, from the perspective of lines B-B of FIG. 38A.

FIG. 39A is a perspective view of a flexible rod for spinal fixation having transverse tunnels within the body of the rod, in accordance with another embodiment of the invention.

FIG. 39B is a cross-sectional view of the flexible rod of FIG. 39A, taken along lines B-B of that figure.

FIG. 39C is an alternative cross-sectional view of the flexible rod of FIG. 39A, taken along lines B-B of that figure, having substantially orthogonal transverse tunnels in the body of the rod, in accordance with a further embodiment of the invention.

DETAILED DESCRIPTION OF THE PREFERRED EMBODIMENTS

The invention is described in detail below with reference to the figures wherein like elements are referenced with like numerals throughout.

Figure 1:
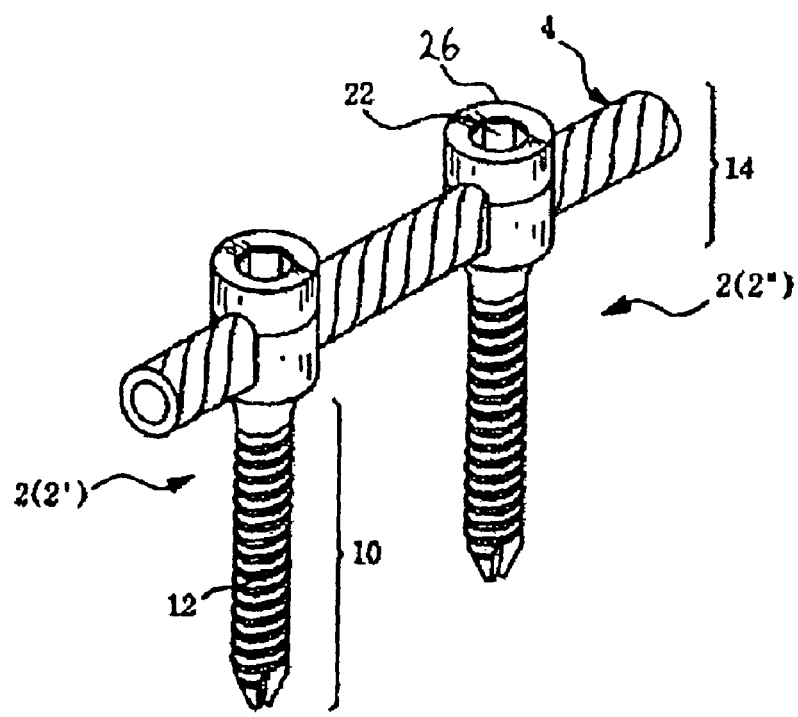
FIG. 1 illustrates a perspective view of a spinal fixation device in accordance with one embodiment of the invention.

FIG. 1 depicts a spinal fixation device in accordance with one embodiment of the present invention. The spinal fixation device includes two securing members 2 (designated as 2' and 2"), and a flexible fixation rod 4 configured to be received and secured within a coupling assembly 14, as described in further detail below with respect to FIG. 3. Each securing member 2 includes a threaded screw-type shaft 10 configured to be inserted and screwed into a patient's spinal pedicle. As shown in FIG. 1, the screw-type shaft 10 includes an external spiral screw thread 12 formed over the length of the shaft 10 and a conical tip at the end of the shaft 10 configured to be inserted into the patient's spinal column at a designated location. Other known forms of the securing member 2 may be used in connection with the present invention provided the securing member 2 can be inserted and fixed into the spinal column and securely coupled to the rod 4.

As described above, the spinal fixation device is used for surgical treatment of spinal diseases by mounting securing members 2 at desired positions in the spinal column. In one embodiment, the rod 4 extends across two or more vertebrae of the spinal column and is secured by the securing members 2 so as to stabilize movement of the two or more vertebrae.

Figure 2:
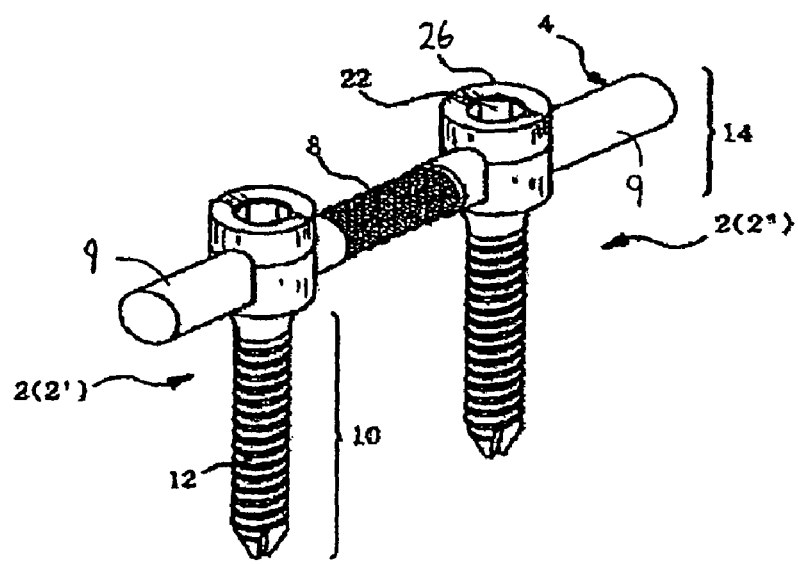
FIG. 2 illustrates a perspective view of spinal fixation device in accordance with another embodiment of the invention.

FIG. 2 illustrates a perspective view of a spinal fixation device in accordance with a further embodiment of the present invention. The spinal fixation device of FIG. 2 is similar to the spinal fixation device of FIG. 1 except that the rod 4 comprises a flexible middle portion 8 juxtaposed between two rigid end portions 9 of the rod 4.

Figure 3:
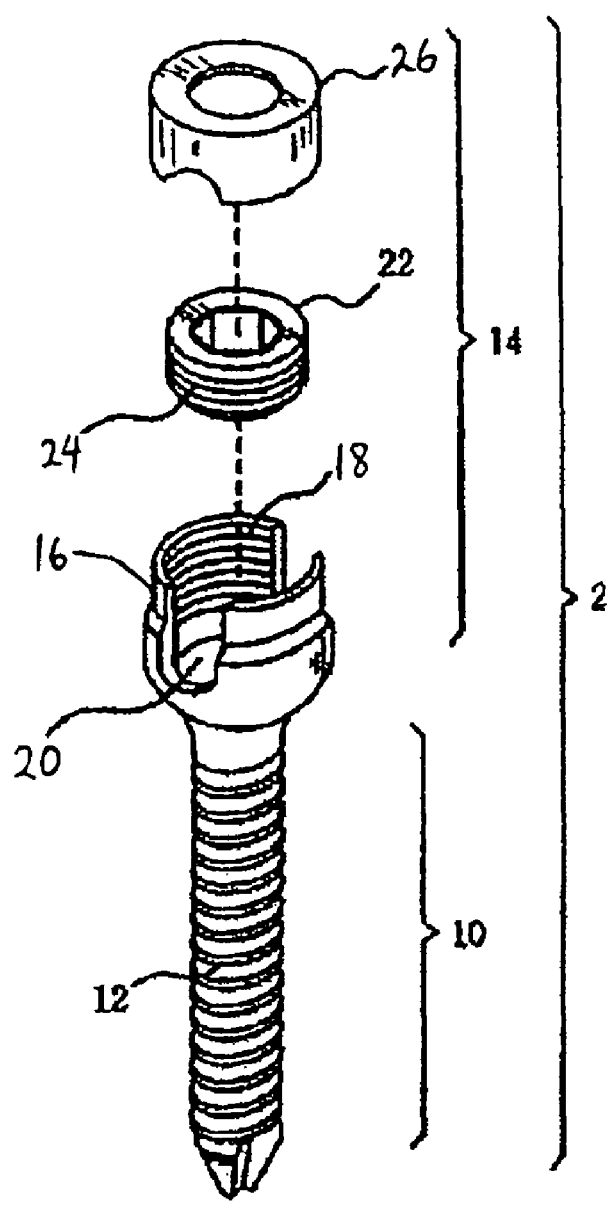
FIG. 3 illustrates an exploded view of the coupling assembly 14 of the pedicle screw 2 of FIGS. 1 and 2, in accordance with one embodiment of the invention.

FIG. 3 provides an exploded view of the securing member 2 of FIGS. 1 and 2 illustrating various components of the coupling assembly 14, in accordance with one embodiment of the invention. As shown in FIG. 3, the coupling assembly 14 includes: a cylindrical head 16 located at a top end of the screw-type shaft 10, a spiral thread or groove 18 formed along portions of the inner wall surface of the cylindrical head 16, and a U-shaped seating groove 20 configured to receive the rod 4 therein. The coupling assembly 14 further comprises an outside-threaded nut 22 having a spiral thread 24 formed on the outside lateral surface of the nut 22, wherein the spiral thread 24 is configured to mate with the internal spiral thread 18 of the cylindrical head 16. In a further embodiment, the coupling assembly 14 includes a fixing cap 26 configured to be mounted over a portion of the cylindrical head 16 to cover and protect the outside-threaded nut 22 and more securely hold rod 4 within seating groove 20. In one embodiment an inner diameter of the fixing gap 26 is configured to securely mate with the outer diameter of the cylindrical head 16. Other methods of securing the fixing cap 26 to the cylindrical head, such as correspondingly located notches and groove (not shown), would be readily apparent to those of skill in the art. In preferred embodiments the components and parts of the securing member 2 may be made of highly rigid and durable bio-compatible materials such as: stainless steel, iron steel, titanium or titanium alloy. Such materials are known in the art. As also known in the art, and used herein, "bio-compatible" materials refers to those materials that will not cause any adverse chemical or immunological reactions after being implanted into a patient's body.

Figure 4:
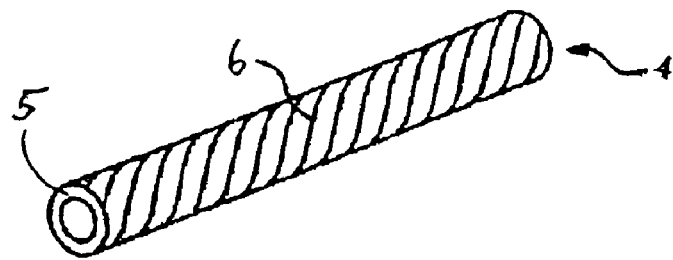
FIG. 4 illustrates a perspective view of a flexible rod connection unit in accordance with one embodiment of the invention.

As shown in FIGS. 1 and 2, in preferred embodiments, the rod 4 is coupled to the securing means 2 by seating the rod 4 horizontally into the seating groove 20 of the coupling means 14 perpendicularly to the direction of the length of the threaded shaft 10 of securing member 2. The outside threaded nut 22 is then received and screwed into the cylindrical head 16 above the rod 4 so as to secure the rod 4 in the seating groove 20. The fixing cap 26 is then placed over the cylindrical head 16 to cover, protect and more firmly secure the components in the internal cavity of the cylindrical head 16. FIGS. 4-7 illustrate perspective views of various embodiments of a rod 4 that may be used in a fixation device, in accordance with the present invention. FIG. 4 illustrates the rod 4 of FIG. 1 wherein the entire rod is made and designed to be flexible. In this embodiment, rod 4 comprises a metal tube or pipe having a cylindrical wall 5 of a predefined thickness. In one embodiment, in order to provide flexibility to the rod 4, the cylindrical wall 5 is cut in a spiral fashion along the length of the rod 4 to form spiral cuts or grooves 6. As would be apparent to one of ordinary skill in the art, the width and density of the spiral grooves 6 may be adjusted to provide a desired level of flexibility. In one embodiment, the grooves 6 are formed from very thin spiral cuts or incisions that penetrate through the entire thickness of the cylindrical wall of the rod 4. As known to those skilled in the art, the thickness and material of the tubular walls 5 also affect the level of flexibility.

In one embodiment, the rod 4 is designed to have a flexibility that substantially equals that of a normal back. Flexibility ranges for a normal back are known by those skilled in the art, and one of ordinary skill can easily determine a thickness and material of the tubular walls 5 and a width and density of the grooves 6 to achieve a desired flexibility or flexibility range within the range for a normal back. When referring to the grooves 6 herein, the term "density" refers to tightness of the spiral grooves 6 or, in other words, the distance between adjacent groove lines 6 as shown in FIG. 4, for example. However, it is understood that the present invention is not limited to a particular, predefined flexibility range. In one embodiment, in addition to having desired lateral flexibility characteristics, the rigidity of the rod 4 should be able to endure a vertical axial load applied to the patient's spinal column along a vertical axis of the spine in a uniform manner with respect to the rest of the patient's natural spine.

Figure 5:
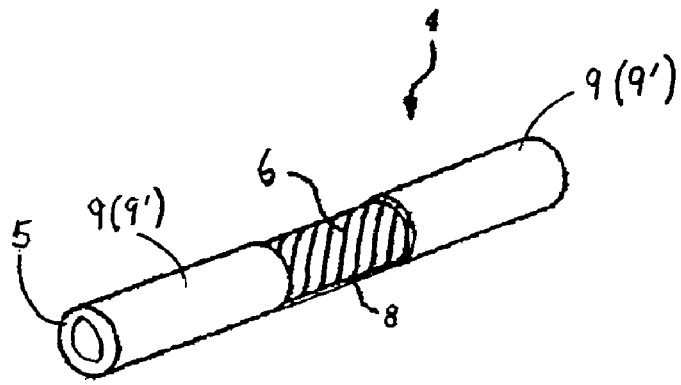
FIG. 5 illustrates a perspective view of a flexible rod connection unit in accordance with another embodiment of the invention.

FIG. 5 illustrates the rod 4 of FIG. 2 wherein only a middle portion 8 is made and designed to be flexible and two end portions 9 are made to be rigid. In one embodiment, metal end rings or caps 9', having no grooves therein, may be placed over respective ends of the rod 4 of FIG. 4 so as make the end portions 9 rigid. The rings or caps 9' may be permanently affixed to the ends of the rod 4 using known methods such as pressing and/or welding the metals together. In another embodiment, the spiral groove 6 is only cut along the length of the middle portion 8 and the end portions 9 comprise the tubular wall 5 without grooves 6. Without the grooves 6, the tubular wall 5, which is made of a rigid metal or metal hybrid material, exhibits high rigidity.

Figure 6:
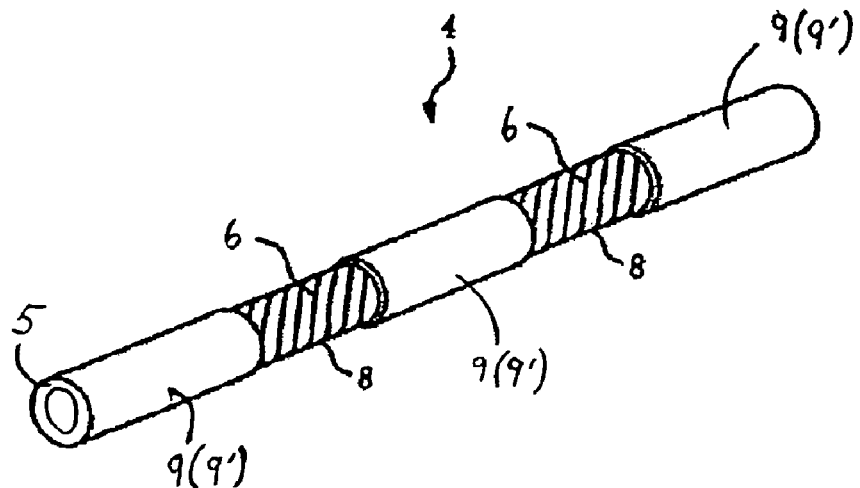
FIG. 6 illustrates a perspective view of a flexible rod connection unit in accordance with a further embodiment of the invention.

FIG. 6 illustrates a further embodiment of the rod 4 having multiple sections, two flexible sections 8 interleaved between three rigid sections 9. This embodiment may be used, for example, to stabilize three adjacent vertebrae with respect to each other, wherein three pedicle screws are fixed to a respective one of the vertebrae and the three rigid sections 9 are connected to a coupling assembly 14 of a respective pedicle screw 2, as described above with respect to FIG. 3. Each of the flexible sections 8 and rigid sections 9 may be made as described above with respect to FIG. 5.

Figure 7:
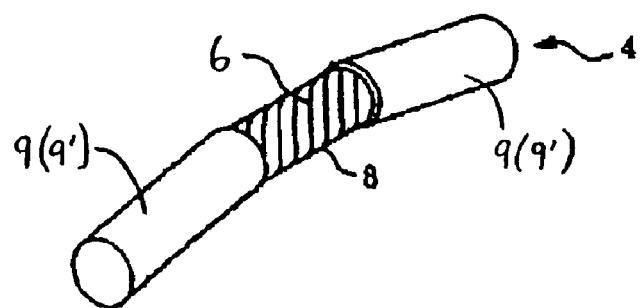
FIG. 7 illustrates a perspective view of a pre-bent flexible rod connection unit in accordance with one embodiment of the invention.

FIG. 7 illustrates another embodiment of the rod 4 having a pre-bent structure and configuration to conform to and maintain a patient's curvature of the spine, known as "lordosis," while stabilizing the spinal column. Generally, a patient's lumbar is in the shape of a 'C' form, and the structure of the rod 4 is formed to coincide to the normal lumbar shape when utilized in the spinal fixation device of FIG. 2, in accordance with one embodiment of the invention. In one embodiment, the pre-bent rod 4 includes a middle portion 8 that is made and designed to be flexible interposed between two rigid end portions 9. The middle portion 8 and end portions 9 may be made as described above with respect to FIG. 5. Methods of manufacturing metallic or metallic-hybrid tubular rods of various sizes, lengths and pre-bent configurations are well-known in the art. Additionally, or alternatively, the pre-bent structure and design of the rod 4 may offset a skew angle when two adjacent pedicle screws are not inserted parallel to one another, as described in further detail below with respect to FIG. 23A.

Figure 8:
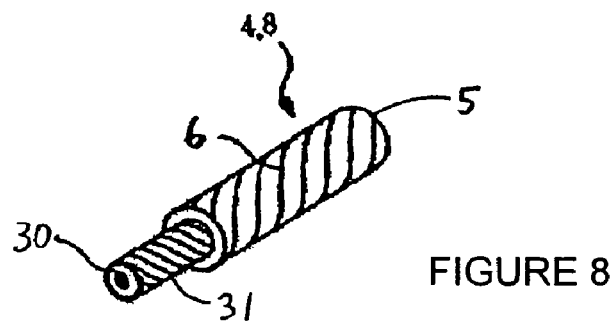
FIG. 8 illustrates a perspective, cross-sectional view of a flexible portion of connection unit in accordance with one embodiment of the invention.

Additional designs and materials used to create a flexible tubular rod 4 or flexible middle portion 8 are described below with respect to FIGS. 8-10. FIG. 8 illustrates a perspective, cross-sectional view of a flexible tubular rod 4, or rod portion 8 in accordance with one embodiment of the invention. In this embodiment, the flexible rod 4, 8 is made from a first metal tube 5 having a spiral groove 6 cut therein as described above with respect to FIGS. 4-7. A second tube 30 having spiral grooves 31 cut therein and having a smaller diameter than the first tube 5 is inserted into the cylindrical cavity of the first tube 5. In one embodiment, the second tube 30 has spiral grooves 31 which are cut in an opposite spiral direction with respect to the spiral grooves 6 cut in the first tube 5, such that the rotational torsion characteristics of the second tube 30 offset at least some of the rotational torsion characteristics of the first tube 5. The second flexible tube 30 is inserted into the core of the first tube to provide further durability and strength to the flexible rod 4, 8. The second tube 30 may be made of the same or different material than the first tube 5. In preferred embodiments, the material used to manufacture the first and second tubes 5 and 30, respectively, may be any one or combination of the following exemplary metals: stainless steel, iron steel, titanium, and titanium alloy.

Figure 9:
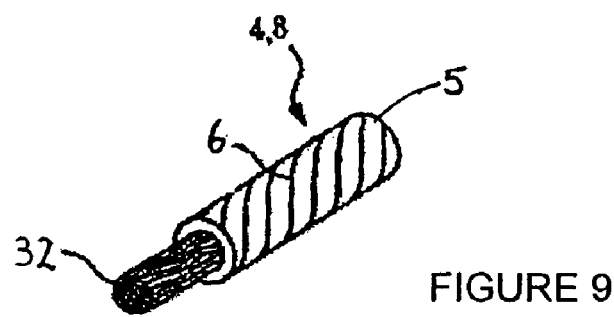
FIG. 9 illustrates a perspective, cross-sectional view of a flexible portion of connection unit in accordance with another embodiment of the invention.

FIG. 9 illustrates a perspective, cross-sectional view of a flexible rod 4, 8 in accordance with a further embodiment of the invention. In this embodiment, the flexible rod 4, 8 includes an inner core made of a metallic wire 32 comprising a plurality of overlapping thin metallic yarns, such as steel yarns, titanium yarns, or titanium-alloy yarns. The wire 32 is encased by a metal, or metal hybrid, flexible tube 5 having spiral grooves 6 cut therein, as discussed above. The number and thickness of the metallic yarns in the wire 32 also affects the rigidity and flexibility of the rod 4, 8. By changing the number, thickness or material of the yarns flexibility can be increased or decreased. Thus, the number, thickness and/or material of the metallic yarns in the wire 32 can be adjusted to provide a desired rigidity and flexibility in accordance with a patient's particular needs. Those of ordinary skill in the art can easily determine the number, thickness and material of the yarns, in conjunction with a given flexibility of the tube 5 in order to achieve a desired rigidity v. flexibility profile for the rod 4, 8.

Figure 10:
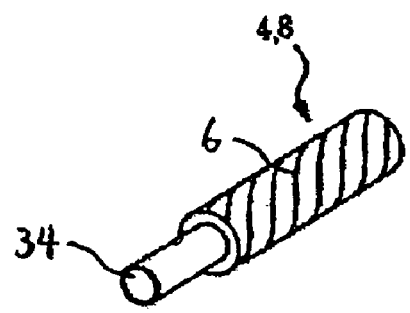
FIG. 10 illustrates a perspective, cross-sectional view of a flexible portion of connection unit in accordance with a further embodiment of the invention.

FIG. 10 shows yet another embodiment of a flexible rod 4 wherein the flexible tube 5 encases a non-metallic, flexible core 34. The core 34 may be made from known biocompatible shape memory alloys (e.g., NITINOL), or biocompatible synthetic materials such as: carbon fiber, Poly Ether Ether Ketone (PEEK), Poly Ether Ketone Ketone Ether Ketone (PEKKEK), or Ultra High Molecular Weight Poly Ethylene (UHMWPE).

Figure 11:
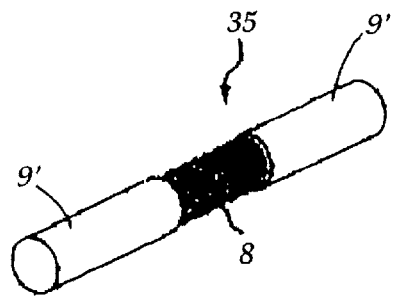
FIG. 11 illustrates a perspective view of a flexible rod connection unit in accordance with one embodiment of the invention.

FIG. 11 illustrates a perspective view of another embodiment of the flexible rod 35 in which a plurality of metal wires 32, as described above with respect to FIG. 9, are interweaved or braided together to form a braided metal wire rod 35. Thus, the braided metal wire rod 35 can be made from the same materials as the metal wire 32. In addition to the variability of the rigidity and flexibility of the wire 32 as explained above, the rigidity and flexibility of the braided rod 35 can be further modified to achieve desired characteristics by varying the number and thickness of the wires 32 used in the braided structure 35. For example, in order to achieve various flexion levels or ranges within the known flexion range of a normal healthy spine, those of ordinary skill in the art can easily manufacture various designs of the braided wire rod 35 by varying and measuring the flexion provided by different gauges, numbers and materials of the wire used to create the braided wire rod 35. In a further embodiment each end of the braided metal wire rod 35 is encased by a rigid metal cap or ring 9' as described above with respect to FIGS. 5-7, to provide a rod 4 having a flexible middle portion 8 and rigid end portions 9. In a further embodiment (not shown), the metal braided wire rod 35 may be utilized as a flexible inner core encased by a metal tube 5 having spiral grooves 6 cut therein to create a flexible metal rod 4 or rod portion 8, in a similar fashion to the embodiments shown in FIGS. 8-10. As used herein the term "braid" or "braided structure" encompasses two or more wires, strips, strands, ribbons and/or other shapes of material interwoven in an overlapping fashion. Various methods of interweaving wires, strips, strands, ribbons and/or other shapes of material are known in the art. Such interweaving techniques are encompassed by the present invention. In another exemplary embodiment (not shown), the flexible metal rod 35 includes a braided metal structure having two or more metal strips, strands or ribbons interweaved in a diagonally overlapping pattern.

Figure 12A:
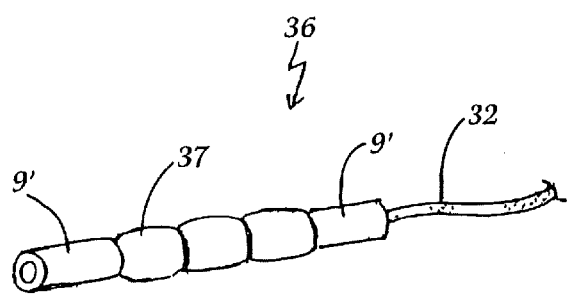
FIG. 12A illustrates a perspective view of a flexible connection unit having one or more spacers in between two end portions, in accordance with one embodiment of the invention.
Figure 12B:
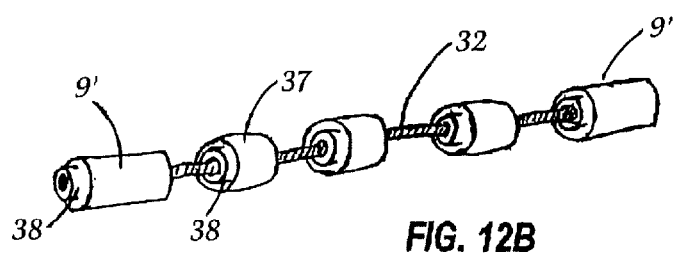
FIG. 12B illustrates an exploded view of the flexible connection unit of FIG. 12A.
Figure 12C:
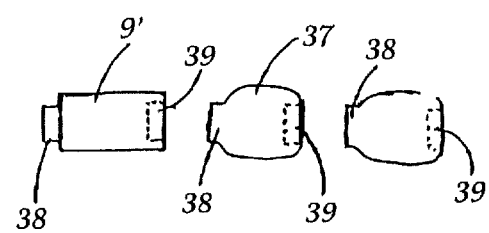
FIG. 12C provides a view of the male and female interlocking elements of the flexible connection unit of FIGS. 12A and 12B, in accordance with one embodiment of the invention.

FIG. 12A illustrates a further embodiment of a flexible connection unit 36 having two rigid end portions 9' and an exemplary number of rigid spacers 37. In one embodiment, the rigid end portions 9' and spacers can be made of biocompatible metal or metal-hybrid materials as discussed above. The connection unit 36 further includes a flexible wire 32, as discussed above with respect to FIG. 9', which traverses an axial cavity or hole (not shown) in each of the rigid end portions 9' and spacers 37. FIG. 12B illustrates an exploded view of the connection unit 36 that further shows how the wire 32 is inserted through center axis holes of the rigid end portions 9' and spacers 37. As further shown in FIG. 12B, each of the end portions 9' and spacers 37 include a male interlocking member 38 which is configured to mate with a female interlocking cavity (not shown) in the immediately adjacent end portion 9' or spacer 37. FIG. 12 C illustrates an exploded side view and indicates with dashed lines the location and configuration of the female interlocking cavity 39 for receiving corresponding male interlocking members 38.

Figure 13:
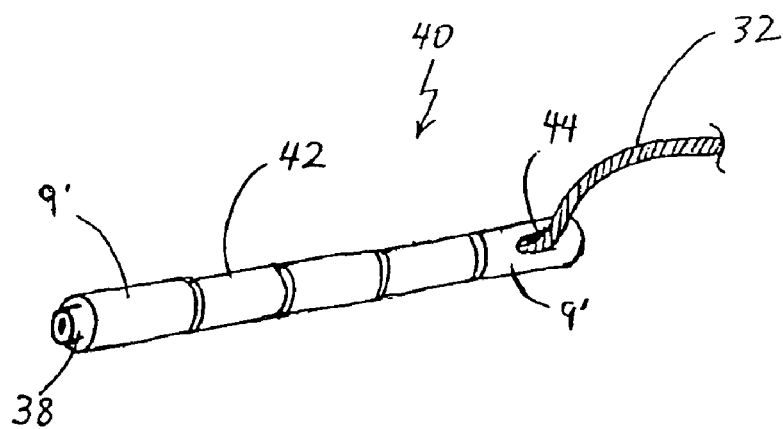
FIG. 13 shows a perspective view of a flexible connection unit, in accordance with a further embodiment of the invention.

FIG. 13 shows a perspective view of a flexible connection unit 40 in accordance with another embodiment of the invention. The connection 40 is similar to the connection unit 36 described above, however, the spacers 42 are configured to have the same shape and design as the rigid end portions 9'. Additionally, the end portions 9' have an exit hole or groove 44 located on a lateral side surface through which the wire 32 may exit, be pulled taut, and clamped or secured using a metal clip (not shown) or other known techniques. In this way, the length of the flexible connection unit 36 or 40 may be varied at the time of surgery to fit each patient's unique anatomical characteristics. In one embodiment, the wire 32 may be secured using a metallic clip or stopper (not shown). For example, a clip or stopper may include a small tubular cylinder having an inner diameter that is slightly larger than the diameter of the wire 32 to allow the wire 32 to pass therethrough. After the wire 32 is pulled to a desired tension through the tubular stopper, the stopper is compressed so as to pinch the wire 32 contained therein. Alternatively, the wire 32 may be pre-secured using known techniques during the manufacture of the rod-like connection units 36, 40 having a predetermined number of spacers 37, 42 therein.

Figure 14:
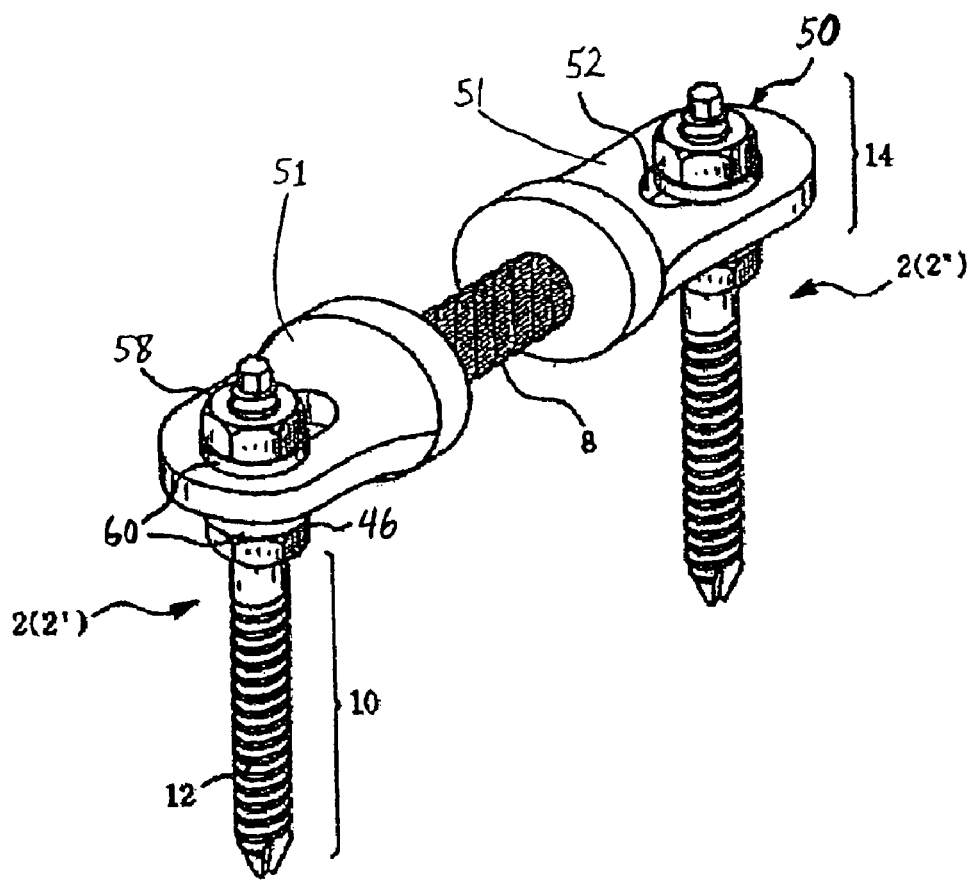
FIG. 14 illustrates a perspective view of a spinal fixation device in accordance with another embodiment of the invention.

FIG. 14 depicts a spinal fixation device according to another embodiment of the present invention. The spinal fixation device includes: at least two securing members 2 containing an elongate screw type shaft 10 having an external spiral thread 12, and a coupling assembly 14. The device further includes a plate connection unit 50, or simply "plate 50," configured to be securely connected to the coupling parts 14 of the two securing members 2. The plate 50 comprises two rigid connection members 51 each having a planar surface and joined to each other by a flexible middle portion 8. The flexible middle portion 8 may be made in accordance with any of the embodiments described above with respect to FIGS. 4-11. Each connection member 51 contains a coupling hole 52 configured to receive therethrough a second threaded shaft 54 (FIG. 15) of the coupling assembly 14.

Figure 15:
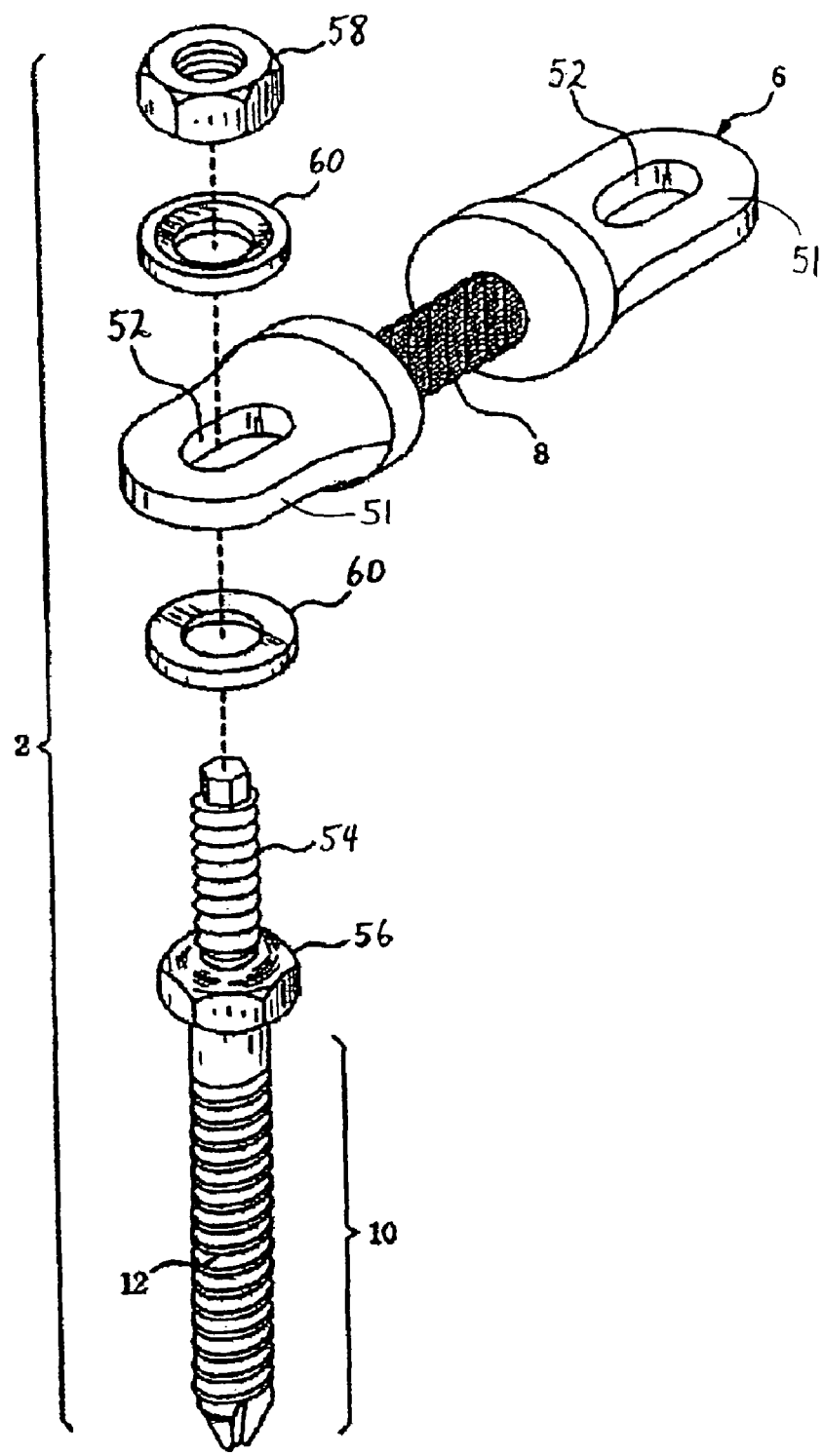
FIG. 15 illustrates an exploded view of the spinal fixation device of FIG. 14.

As shown in FIG. 15, the coupling assembly 14 of the securing member 2 includes a bolt head 56 adjoining the top of the first threaded shaft 10 and having a circumference or diameter greater than the circumference of the first threaded shaft 10. The second threaded shaft 54 extends upwardly from the bolt head 56. The coupling assembly 14 further includes a nut 58 having an internal screw thread configured to mate with the second threaded shaft 54, and one or more washers 60, for clamping the connection member 51 against the top surface of the bolt head 56, thereby securely attaching the plate 50 to the pedicle screw 2.

Figure 16A:
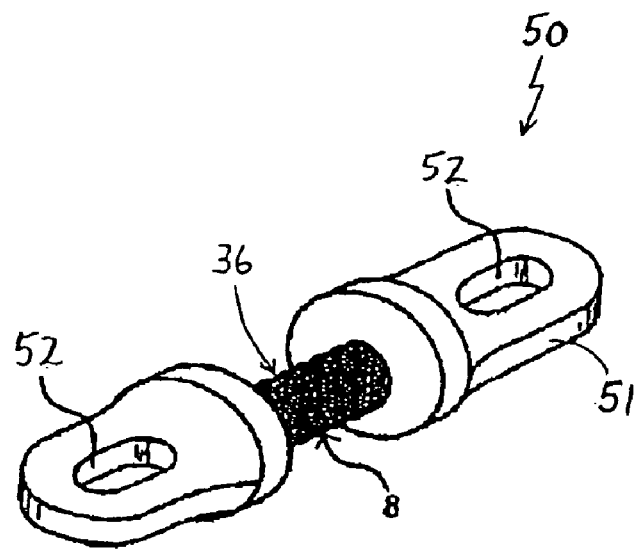
FIG. 16A shows a perspective view of a flexible plate connection unit in accordance with one embodiment of the invention.
Figure 16B:
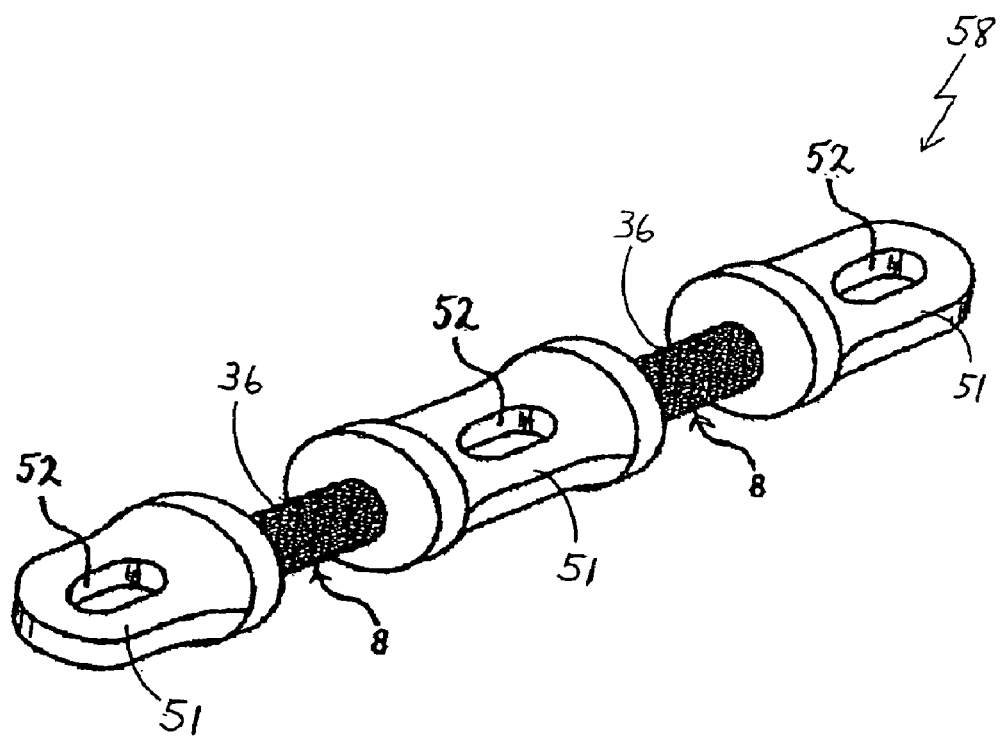
FIG. 16B illustrates a perspective view of a flexible plate connection unit in accordance with a further embodiment of the invention.
Figure 16C:
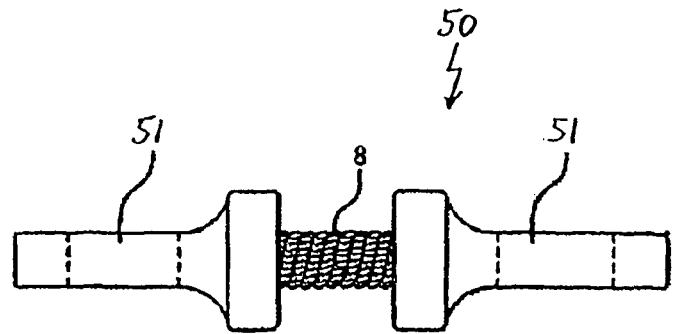
FIG. 16C shows a side view of the flexible plate connection unit of FIG. 16A.
Figure 16D:
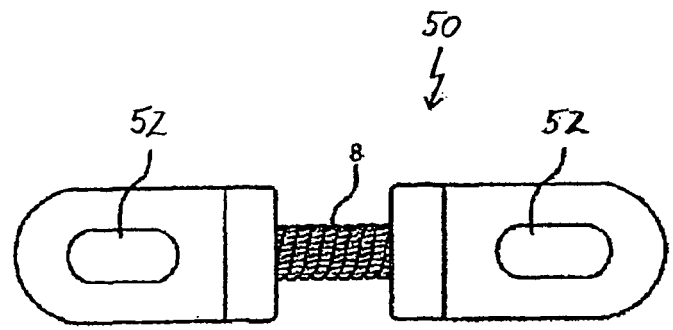
FIG. 16D shows a top view of the flexible plate connection unit of FIG. 16A.

FIGS. 16A and 16B illustrate two embodiments of a plate connection unit 40 having at least two coupling members 51 and at least one flexible portion 8 interposed between and attached to two adjacent connection members 51. As shown in FIGS. 16A and 16B, the flexible middle portion 8 comprises a flexible metal braided wire structure 36 as described above with respect to FIG. 11. However, the flexible portion 8 can be designed and manufactured in accordance with any of the embodiments described above with respect to FIGS. 4-11, or combinations thereof. FIGS. 16C and 16D illustrate a side view and top view, respectively, of the plate 50 of FIG. 16A. The manufacture of different embodiments of the flexible connection units 50 and 58 having different types of flexible middle portions 8, as described above, is easily accomplished using known metallurgy manufacturing processes.

Figure 16E:
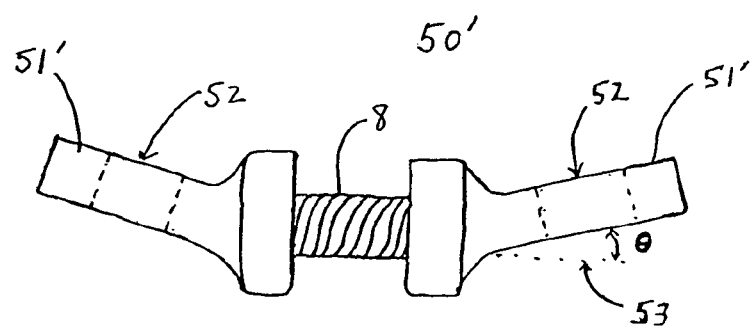
FIG. 16E illustrates a side view of the flexible plate connection unit of FIG. 16A having a pre-bent configuration in accordance with a further embodiment of the invention.

FIG. 16E illustrate a side view of a pre-bent plate connection unit 50', in accordance with a further embodiment of the invention. This plate connection unit 50' is similar to the plate 50 except that connection members 51' are formed or bent at an angle θ from a parallel plane 53 during manufacture of the plate connection unit 50'. As discussed above with respect to the pre-bent rod-like connection unit 4 of FIG. 7, this pre-bent configuration is designed to emulate and support a natural curvature of the spine (e.g., lordosis). Additionally, or alternatively, this pre-bent structure may offset a skew angle when two adjacent pedicle screws are not inserted parallel to one another, as described in further detail below with respect to FIG. 23A.

Figure 17:
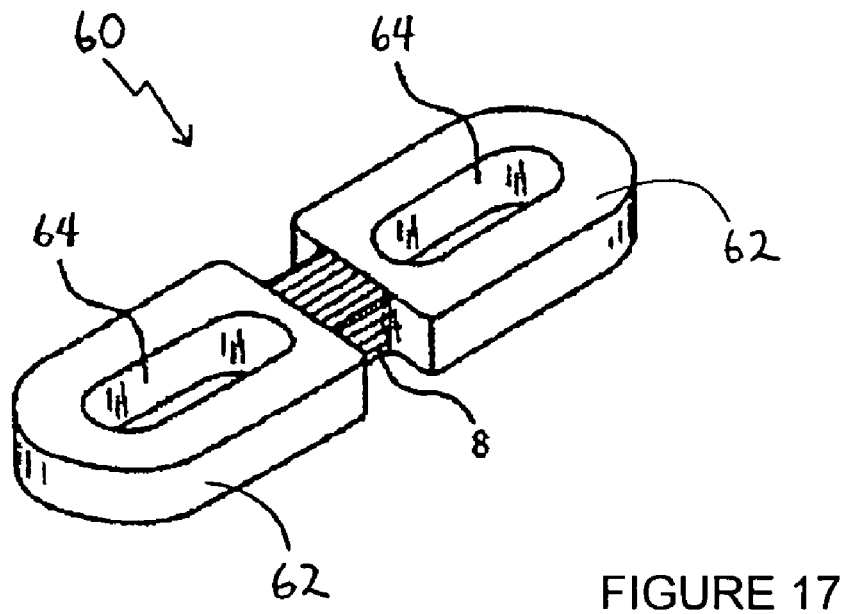
FIG. 17 is a perspective view of a flexible plate connection unit in accordance with another embodiment of the invention.

FIG. 17 illustrates a perspective view of a plate connection unit 60 having two planar connection members 62 each having a coupling hole 64 therein for receiving the second threaded shaft 44 of the pedicle screw 2. A flexible middle portion 8 is interposed between the two connection members 62 and attached thereto. In one embodiment, the flexible middle portion 8 is made in a similar fashion to wire 32 described above with respect to FIG. 9, except it has a rectangular configuration instead of a cylindrical or circular configuration as shown in FIG. 9. It is understood, however, that the flexible middle portion 8 may be made in accordance with the design and materials of any of the embodiments previously discussed.

Figure 18:
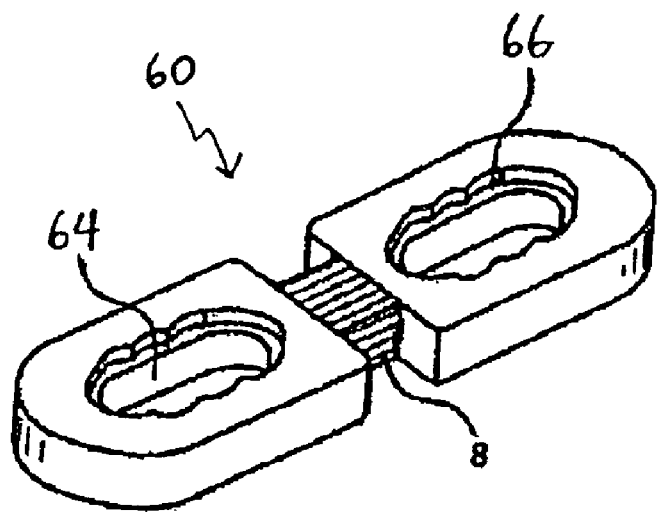
FIG. 18 illustrates a perspective view of a flexible plate connection unit in accordance with another embodiment of the invention.

FIG. 18 illustrates a perspective view of a further embodiment of the plate 60 of FIG. 17 wherein the coupling hole 64 includes one or more nut guide grooves 66 cut into the top portion of the connection member 62 to seat and fix the nut 58 (FIG. 15) into the coupling hole 64. The nut guide groove 66 is configured to receive and hold at least a portion of the nut 58 therein and prevent lateral sliding of the nut 58 within the coupling hole 64 after the connection member 62 has been clamped to the bolt head 56 of the pedicle screw 2.

Figure 19:
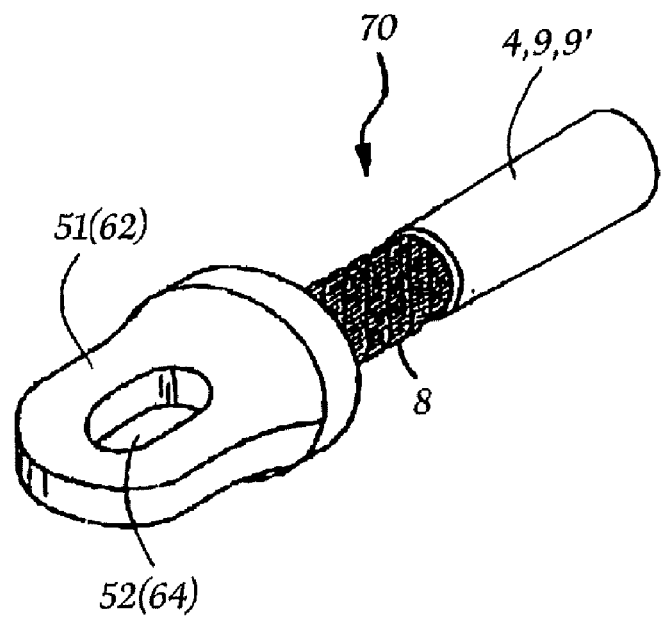
FIG. 19 illustrates a perspective view of a hybrid rod-plate connection unit having a flexible middle portion according to a further embodiment of the present invention.

FIG. 19 illustrates a perspective view of a hybrid plate and rod connection unit 70 having a rigid rod-like connection member 4, 9 or 9', as described above with respect to FIGS. 4-7, at one end of the connection unit 70 and a plate-like connection member 51 or 62, as described above with respect to FIGS. 14-18, at the other end of the connection unit 70. In one embodiment, interposed between rod-like connection member 9 (9') and the plate-like connection member 52 (64) is a flexible member 8. The flexible member 8 may be designed and manufactured in accordance with any of the embodiments discussed above with reference to FIGS. 8-13.

Figure 20:
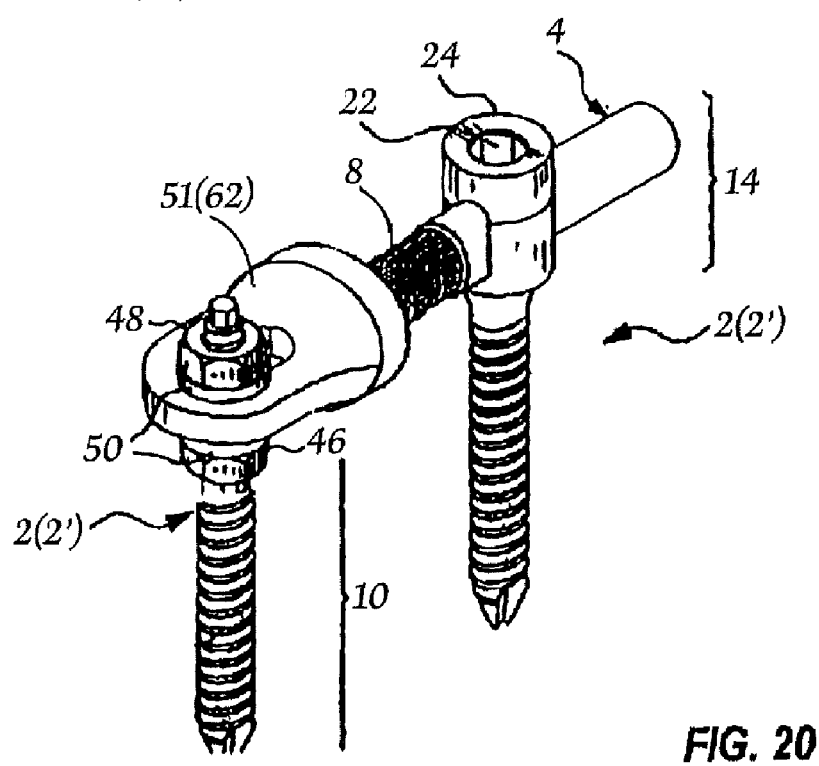
FIG. 20 is a perspective view of a spinal fixation device that utilizes the hybrid rod-plate connection unit of FIG. 19.

FIG. 20 illustrates a perspective view of a spinal fixation device that utilizes the hybrid plate and rod connection unit 70 of FIG. 19. As shown in FIG. 20, this fixation device utilizes two types of securing members 2 (e.g., pedicle screws), the first securing member 2' being configured to securely hold the plate connection member 42(64) as described above with respect to FIG. 15, and the second securing member 2" being configured to securely hold the rod connection member 4, 9 or 9', as described above with respect to FIG. 3.

FIG. 21 illustrates a perspective top view of two spinal fixation devices, in accordance with the embodiment illustrated in FIG. 1, after they are attached to two adjacent vertebrae 80 and 82 to flexibly stabilize the vertebrae. FIGS. 22A and 22B illustrate perspective top views of spinal fixation devices using the flexible stabilizing members 50 and 58 of FIGS. 16A and 16B, respectively, after they are attached to two or more adjacent vertebrae of the spine.

Figure 23A:
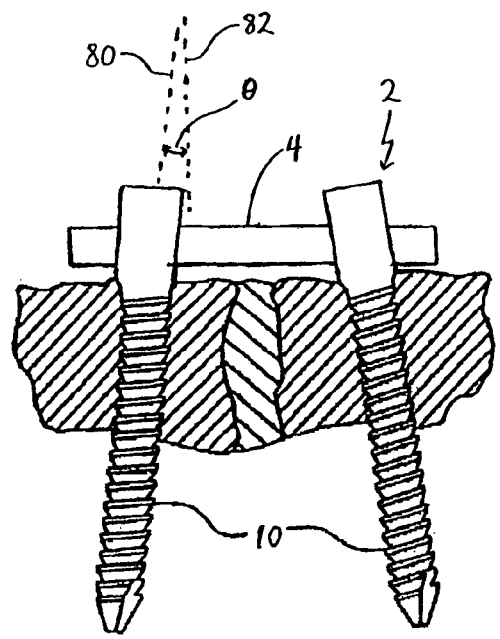
FIG. 23A illustrates a perspective view of two pedicle screws inserted into the pedicles of two adjacent vertebrae at a skewed angle, in accordance with one embodiment of the invention.

FIG. 23A illustrates a side view of a spinal fixation device after it has been implanted into the pedicles of two adjacent vertebrae. As shown in this figure, the pedicle screws 2 are mounted into the pedicle bone such that a center axis 80 of the screws 2 are offset by an angle θ from a parallel plane 82 and the center axes 80 of the two screws 2 are offset by an angle of approximately 2θ from each other. This type of non-parallel insertion of the pedicle screws 2 often results due to the limited amount of space that is available when performing minimally invasive surgery. Additionally, the pedicle screws 2 may have a tendency to be skewed from parallel due to a patient's natural curvature of the spine (e.g., lordosis). Thus, due to the non-parallel nature of how the pedicle screws 2 are ultimately fixed to the spinal pedicle, it is desirable to offset this skew when attaching a rod or plate connection unit to each of the pedicle screws 2.

Figure 23B:
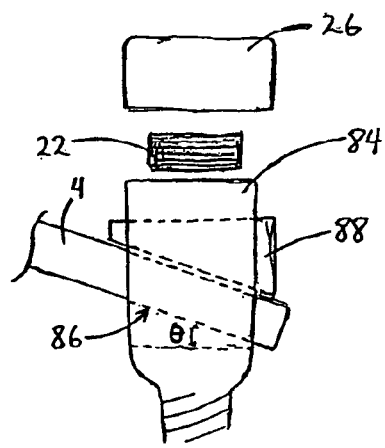
FIG. 23B illustrates a structural view of a coupling assembly of a pedicle screw in accordance with one embodiment of the invention.

FIG. 23B illustrates a side view of the head of the pedicle screw in accordance with one embodiment of the invention. The screw 2 includes a cylindrical head 84 which is similar to the cylindrical head 16 described above with respect to FIG. 3 except that the cylindrical head 84 includes a slanted seat 86 configured to receive and hold a flexible rod 4 in a slanted orientation that offsets the slant or skew θ of the pedicle screw 2 as described above. The improved pedicle screw 2 further includes a slanted stabilizing spacer 88 which is configured to securely fit inside the cavity of the cylindrical head 84 and hold down the rod 4 at the same slant as the slanted seat 86. The pedicle screw 2 further includes an outside threaded nut 22 configured to mate with spiral threads along the interior surface (not shown) of the cylindrical head 84 for clamping down and securing the slanted spacer 88 and the rod 4 to the slanted seat 86 and, hence, to the cylindrical head 84 of the pedicle screw 2.

Figure 23C:
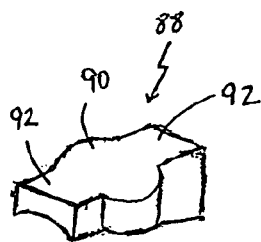
FIG. 23C provides a perspective view of a slanted stabilizing spacer in accordance with one embodiment of the invention.
Figure 23D:
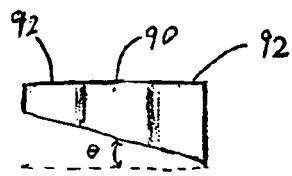
FIG. 23D illustrates a side view of the slanted stabilizing spacer of FIG. 23C.
Figure 23E:
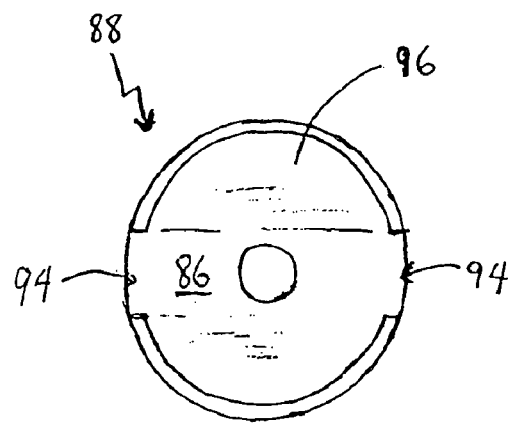
FIG. 23E is a top view of the cylindrical head of the pedicle screw of FIG. 23.

FIG. 23C shows a perspective view of the slanted spacer 88, in accordance with embodiment of the invention. The spacer 88 includes a circular middle portion 90 and two rectangular-shaped end portions 92 extending outwardly from opposite sides of the circular middle portion 90. FIG. 23D shows a side view of the spacer 88 that further illustrates the slant from one end to another to compensate or offset the skew angle θ of the pedicle screw 2. FIG. 23E illustrates a top view of the cylindrical head 84 configured to receive a rod 4 and slanted spacer 88 therein. The rod 4 is received through two openings or slots 94 in the cylindrical walls of the cylindrical head 84, which allow the rod 4 to enter the circular or cylindrical cavity 96 of the cylindrical head 84 and rest on top of the slanted seat 86 formed within the circular or cylindrical cavity 94. After the rod 4 is positioned on the slanted seat 86, the slanted stabilizing spacer 88 is received in the cavity 96 such that the two rectangular-shaped end portions 92 are received within the two slots 94, thereby preventing lateral rotation of the spacer 88 within the cylindrical cavity 96. Finally, the outside threaded nut 22 and fixing cap 26 are inserted on top of the slanted spacer 88 to securely hold the spacer 88 and rod 4 within the cylindrical head 84.

Figure 24:
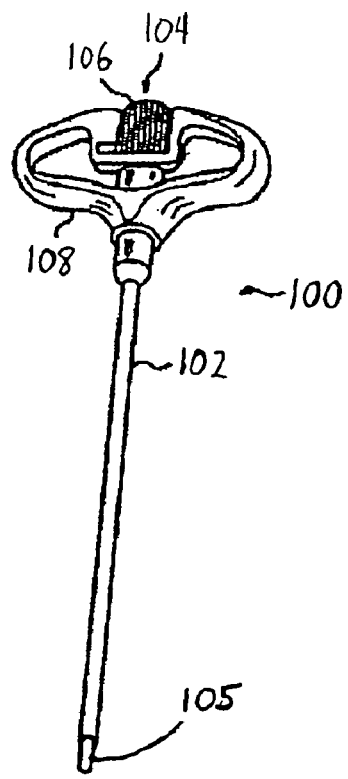
FIG. 24 illustrates a perspective view of a marking and guiding device in accordance with one embodiment of the invention.

FIG. 24 illustrates a perspective view of a marking and guidance device 100 for marking a desired location on the spinal pedicle where a pedicle screw 2 will be inserted and guiding the pedicle screw 2 to the marked location using a minimally invasive surgical technique. As shown in FIG. 24, the marking device 100 includes a tubular hollow guider 52 which receives within its hollow an inner trocar 104 having a sharp tip 105 at one end that penetrates a patient's muscle and tissue to reach the spinal pedicle. the inner trocar 104 further includes a trocar grip 106 at the other end for easy insertion and removal of the trocar 104. In one embodiment, the marking and guidance device 100 includes a guider handle 108 to allow for easier handling of the device 100.

Figure 25:
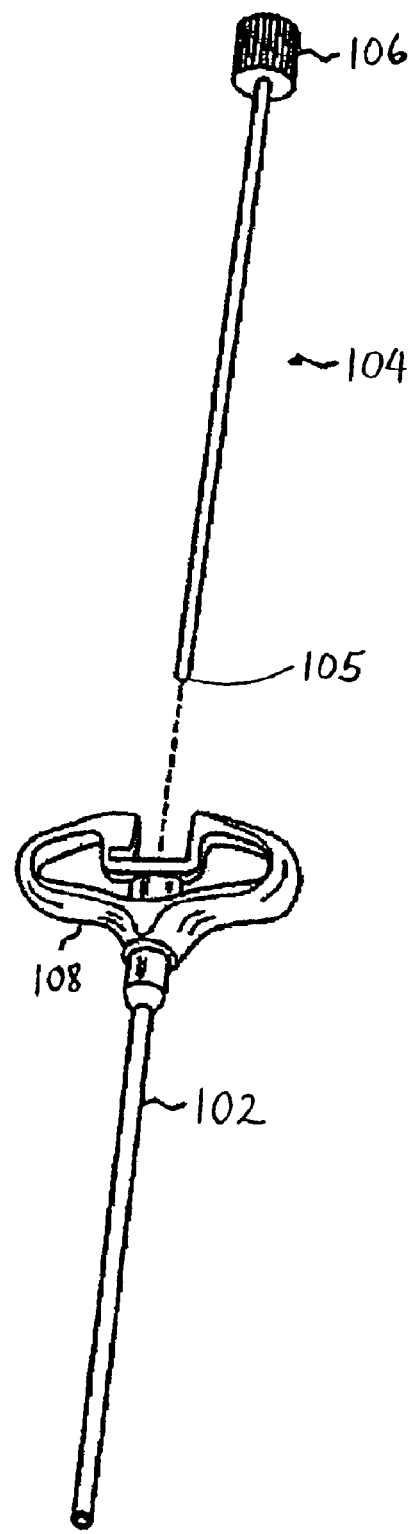
FIG. 25 is an exploded view of the marking and guidance device of FIG. 24.

As shown in FIG. 25, the trocar 104 is in the form of a long tube or cylinder having a diameter smaller than the inner diameter of the hollow of the guider 102 so as to be inserted into the hollow of the tubular guider 102. The trocar 104 further includes a sharp or pointed tip 105 for penetrating the vertebral body through the pedicle. The trocar 104 further includes a trocar grip 106 having a diameter larger than the diameter of the hollow of the guider tube 102 in order to stop the trocar 104 from sliding completely through the hollow. The trocar grip 106 also allows for easier handling of the trocar 104.

Figure 26A:
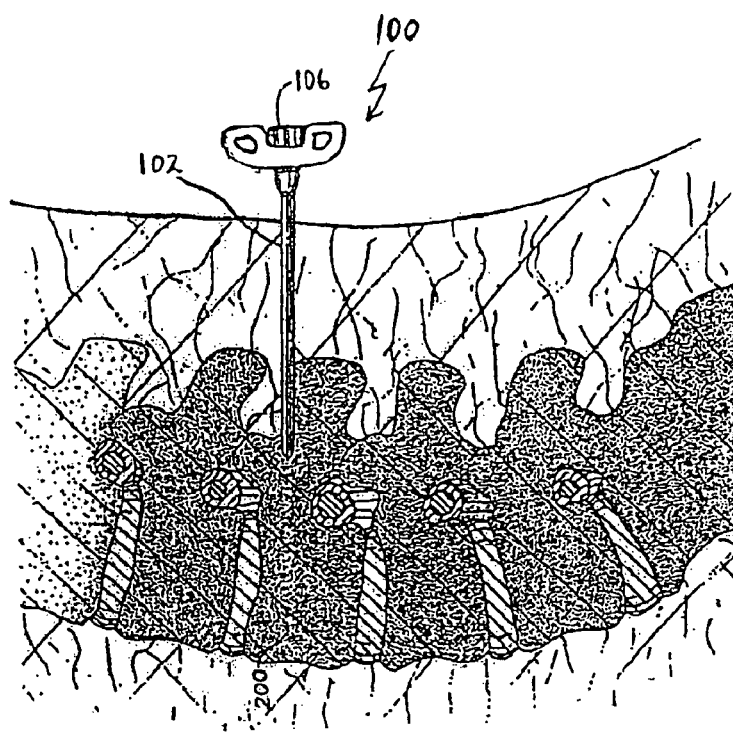
FIG. 26A provides a perspective, cross-section view of a patient's spine after the marking and guiding device of FIG. 24 has been inserted during surgery.
Figure 26B:
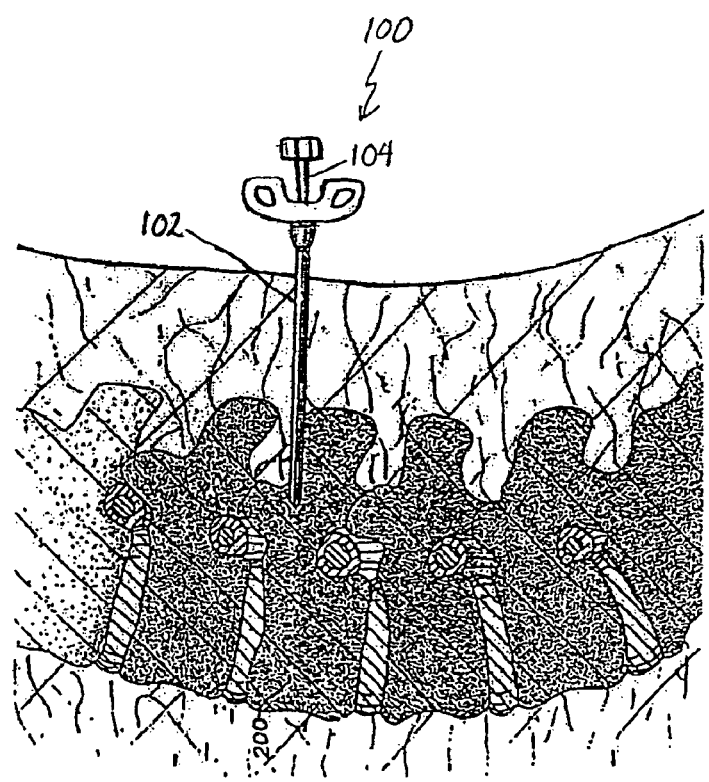
FIG. 26B provides a perspective, cross-section view of a patient's spine as an inner trocar of the marking and guiding device of FIG. 24 is being removed.

FIGS. 26A and 26B provide perspective views of the marking and guidance device 100 after it has been inserted into a patient's back and pushed through the muscle and soft tissue to reach a desired location on the spinal pedicle. The desired location is determined using known techniques such as x-ray or radiographic imaging for a relatively short duration of time. After the marking and guidance device 100 has been inserted, prolonged exposure of the patient to x-ray radiation is unnecessary. As shown in FIG. 26B, after the guidance tube 102 is positioned over the desired location on the pedicle, the inner trocar 104 is removed to allow fiducial pins (not shown) to be inserted into the hollow of the guidance tube 102 and thereafter be fixed into the pedicle.

FIGS. 27A and 27B illustrate perspective views of two embodiments of the fiducial pins 110 and 112, respectively. As mentioned above, the fiducial pins 110 and 112 according to the present invention are inserted and fixed into the spinal pedicle after passing through the hollow guider 102. The pins 110 and 112 have a cylindrical shape with a diameter smaller than the inner diameter of the hollow of the guider tube 102 in order to pass through the hollow of the guider 102. An end of each fiducial pin is a sharp point 111 configured to be easily inserted and fixed into the spinal pedicle of the spinal column. In one embodiment, as shown in FIG. 27B, the other end of the fiducial pin incorporates a threaded shaft 114 which is configured to mate with an internally threaded tube of a retriever (not shown) for extraction of the pin 112. This retriever is described in further detail below with respect to FIG. 32.

The fiducial pins 110, 112 are preferably made of a durable and rigid biocompatible metal (e.g., stainless steel, iron steel, titanium, titanium alloy) for easy insertion into the pedicle bone. In contrast to prior art guide wires, because of its comparatively shorter length and more rigid construction, the fiducial pins 110, 112 are easily driven into the spinal pedicle without risk of bending or structural failure. As explained above, the process of driving in prior art guidance wires was often very difficult and time-consuming. The insertion of the fiducial pins 110, 112 into the entry point on the spinal pedicle is much easier and convenient for the surgeon and, furthermore, does not hinder subsequent procedures due to a guide wire protruding out of the patient's back.

FIG. 28 shows a cylindrical pushing trocar 116 having a cylindrical head 118 of larger diameter than the body of the pushing trocar 116. The pushing trocar 116, according to the present invention, is inserted into the hollow of the guider 102 after the fiducial pin 110 or 112 has been inserted into the hollow of the guider 102 to drive and fix the fiducial pin 110 or 112 into the spinal pedicle. During this pin insertion procedure, a doctor strikes the trocar head 118 with a chisel or a hammer to drive the fiducial pin 110 and 112 into the spinal pedicle. In preferred embodiments, the pushing trocar 116 is in the form of a cylindrical tube, which has a diameter smaller than the inner diameter of the hollow of the guider tube 112. The pushing trocar 116 also includes a cylindrical head 118 having a diameter larger than the diameter of the pushing trocar 116 to allow the doctor to strike it with a chisel or hammer with greater ease. Of course, in alternative embodiments, a hammer or chisel is not necessarily required. For example, depending on the circumstances of each case, a surgeon may choose to push or tap the head 118 of the pushing trocar 116 with the palm of his or her hand or other object.

Figure 29A:
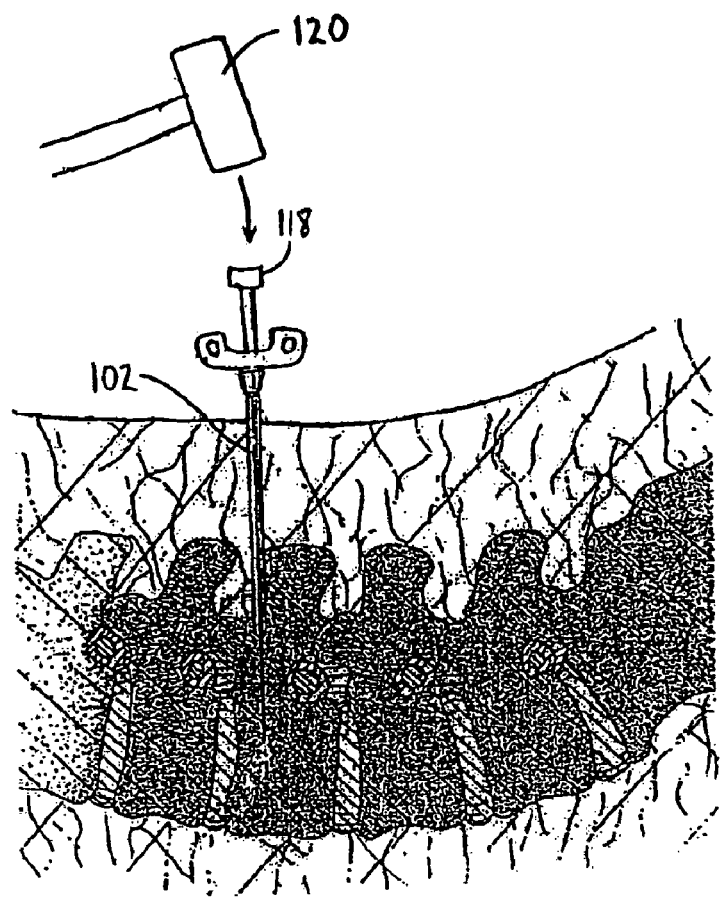
FIG. 29A illustrates a perspective, cross-sectional view of a patient's spine as the pushing trocar of FIG. 28 is used to drive a fiducial pin into a designate location of a spinal pedicle, in accordance with one embodiment of the invention.
Figure 29B:
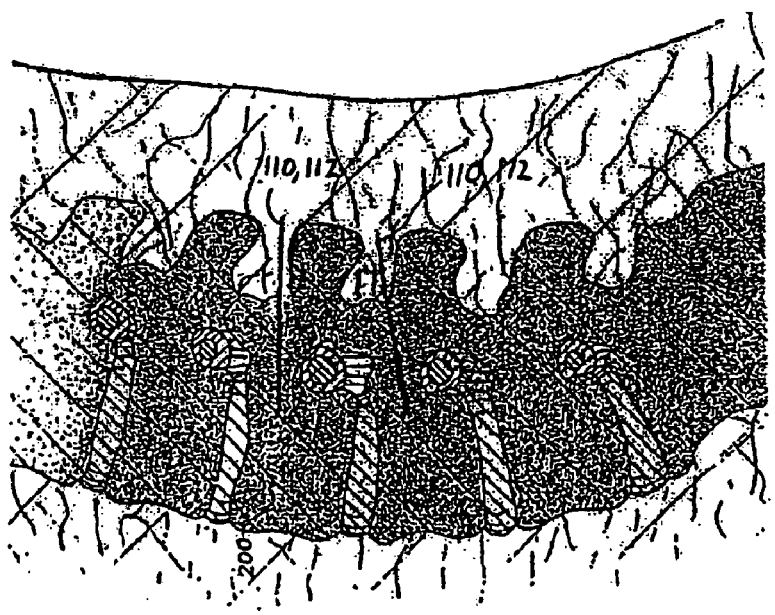
FIG. 29B illustrates a perspective, cross-sectional view of a patient's spine after two fiducial pins have been implanted into two adjacent spinal pedicles, in accordance with one embodiment of the invention.

FIG. 29A illustrates how a hammer or mallet 120 and the pushing trocar 116 may be used to drive the pin 110, 112 through the hollow of the guider tube 102 and into the designated location of the spinal pedicle. FIG. 29B illustrates a perspective cross-sectional view of the spinal column after two fiducial pins 110, 112 have been driven and fixed into two adjacent vertebrae.

Figure 30:
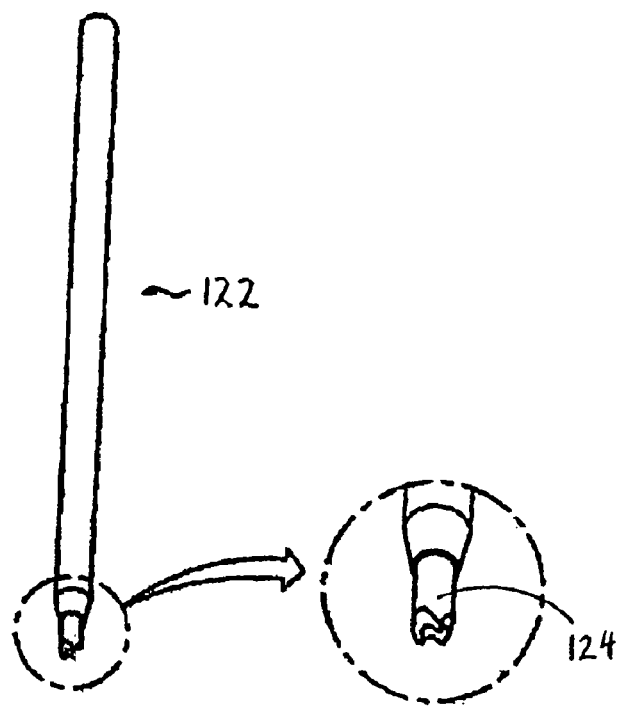
FIG. 30 is a perspective view of a cannulated awl in accordance with one embodiment of the invention.
Figure 31:
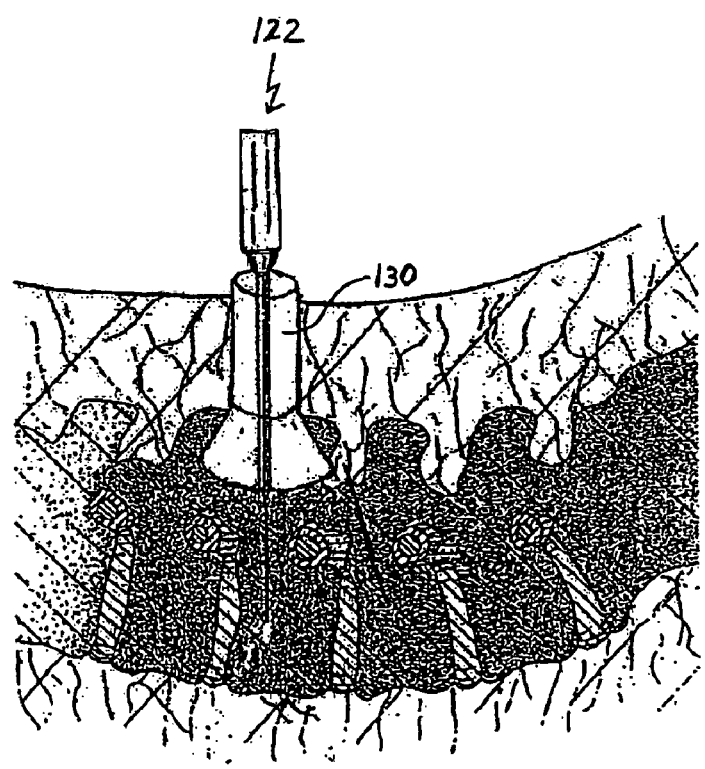
FIG. 31 is a perspective, cross-sectional view of a patient's spine as the cannulated awl of FIG. 30 is being used to enlarge an entry hole for a pedicle screw, in accordance with one embodiment of the invention.

After the fiducial pins 110 or 112 have been inserted into the spinal pedicle as discussed above, in one embodiment, a larger hole or area centered around each pin 110, 112 is created to allow easer insertion and mounting of a pedicle screw 2 into the pedicle bone. The larger hole is created using a cannulated awl 122 as shown in FIG. 30. The cannulated awl 122 is inserted over the fiducial pin 110, 112 fixed at the desired position of the spinal pedicle. The awl 122 is in the form of a cylindrical hollow tube wherein an internal diameter of the hollow is larger than the outer diameter of the fiducial pins 110 and 112 so that the pins 110, 112 may be inserted into the hollow of the awl 122. The awl 122 further includes one or more sharp teeth 124 at a first end for cutting and grinding tissue and bone so as to create the larger entry point centered around the fiducial pin 110, 112 so that the pedicle screw 2 may be more easily implanted into the spinal pedicle. FIG. 31 illustrates a perspective cross-sectional view of a patient's spinal column when the cannulated awl 122 is inserted into a minimally invasive incision in the patient's back, over a fiducial pin 110, 112 to create a larger insertion hole for a pedicle screw 2 (not shown). As shown in FIG. 31, a retractor 130 has been inserted into the minimally invasive incision over the surgical area and a lower tubular body of the retractor 130 is expanded to outwardly push surrounding tissue away from the surgical area and provide more space and a visual field for the surgeon to operate. In order to insert the retractor 130, in one embodiment, the minimally invasive incision is made in the patient's back between and connecting the two entry points of the guide tube 102 used to insert the two fiducial pins 110, 112. Before the retractor 130 is inserted, prior expansion of the minimally invasive incision is typically required using a series of step dilators (not shown), each subsequent dilator having a larger diameter than the previous dilator. After the last step dilator is in place, the retractor 130 is inserted with its lower tubular body in a retracted, non-expanded state. After the retractor 130 is pushed toward the spinal pedicle to a desired depth, the lower tubular portion is then expanded as shown in FIG. 31. The use of step dilators and retractors are well known in the art.

Figure 32:
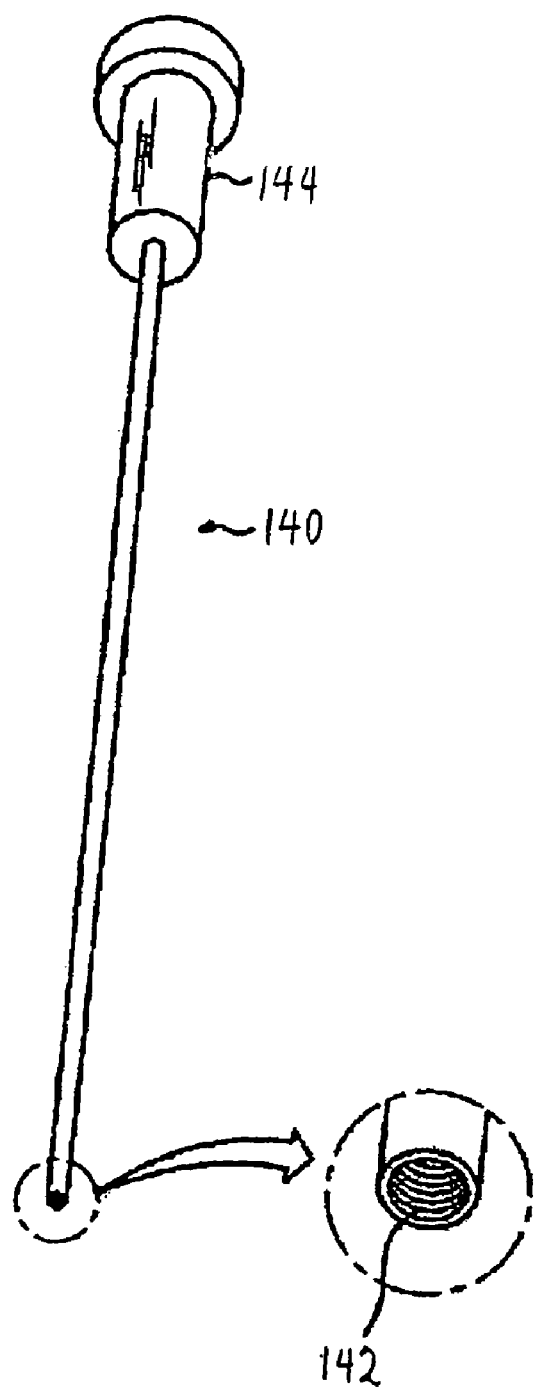
FIG. 32 provides a perspective view of fiducial pin retrieving device, in accordance with one embodiment of the invention.

After the cannulated awl 122 has created a larger insertion hole for the pedicle screw 2, in one embodiment, the fiducial pin 110, 112 is removed. As discussed above, if the fiducial pin 112 has been used, a retrieving device 140 may be used to remove the fiducial pin 112 before implantation of a pedicle screw 2. As shown in FIG. 32, the retriever 140 comprises a long tubular or cylindrical portion having an internally threaded end 142 configured to mate with the externally threaded top portion 114 of the fiducial pin 112. After the retriever end 142 has been screwed onto the threaded end 114, a doctor my pull the fiducial pin 112 out of the spinal pedicle. In another embodiment, if the fiducial pin 110 without a threaded top portion has been used, appropriate tools (e.g., specially designed needle nose pliers) may be used to pull the pin 110 out.

Figure 33:
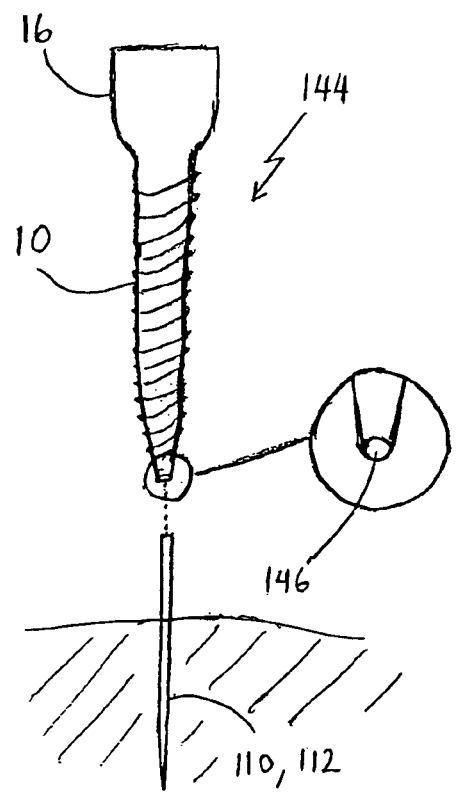
FIG. 33 is a perspective view of a pedicle screw having an axial cylindrical cavity for receiving at least a portion of a fiducial pin therein, in accordance with a further embodiment of the invention.

In alternate embodiments, the fiducial pins 110, 112 are not extracted from the spinal pedicle. Instead, a specially designed pedicle screw 144 may be inserted into the spinal pedicle over the pin 110, 112 without prior removal of the pin 110, 112. As shown in FIG. 33, the specially designed pedicle screw 144 includes an externally threaded shaft 10 and a coupling assembly 14 (FIG. 3) that includes a cylindrical head 16 (FIG. 3) for receiving a flexible rod-shaped connection unit 4 (FIGS. 4-13). Alternatively, the coupling assembly 14 may be configured to receive a plate-like connection unit as shown in FIGS. 14-20. The pedicle screw 144 further includes a longitudinal axial channel (not shown) inside the threaded shaft 10 having an opening 146 at the tip of the shaft 10 and configured to receive the fiducial pin 110, 112 therein.

Figure 34:
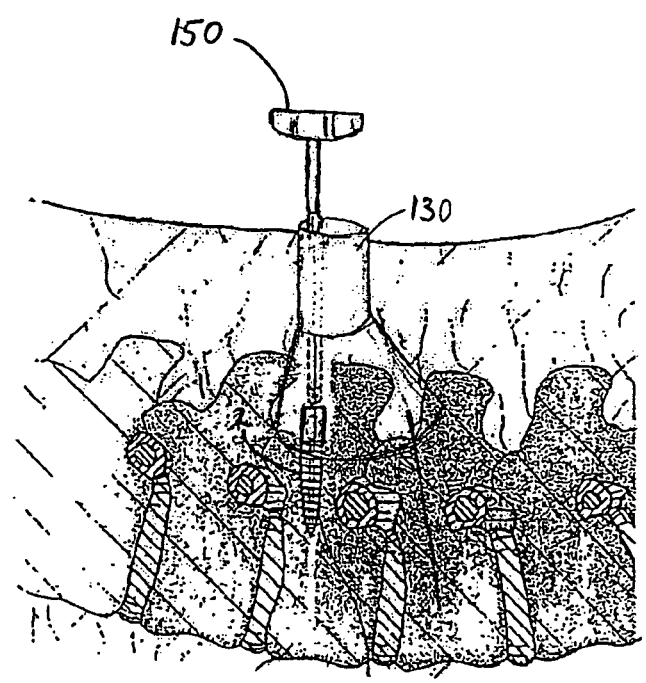
FIG. 34 is a perspective, cross-sectional view of a patient's spine after one pedicle screw has been implanted into a designated location of a spinal pedicle, in accordance with one embodiment of the invention.

FIG. 34 illustrates a perspective cross-sectional view of the patient's spinal column after a pedicle screw 2 has been inserted into a first pedicle of the spine using an insertion device 150. Various types of insertion devices 150 known in the art may be used to insert the pedicle screw 2. As shown in FIG. 34, after a first pedicle screw 2 has been implanted, the retractor 130 is adjusted and moved slightly to provide space and a visual field for insertion of a second pedicle screw at the location of the second fiducial pin 110, 112.

Figure 35:
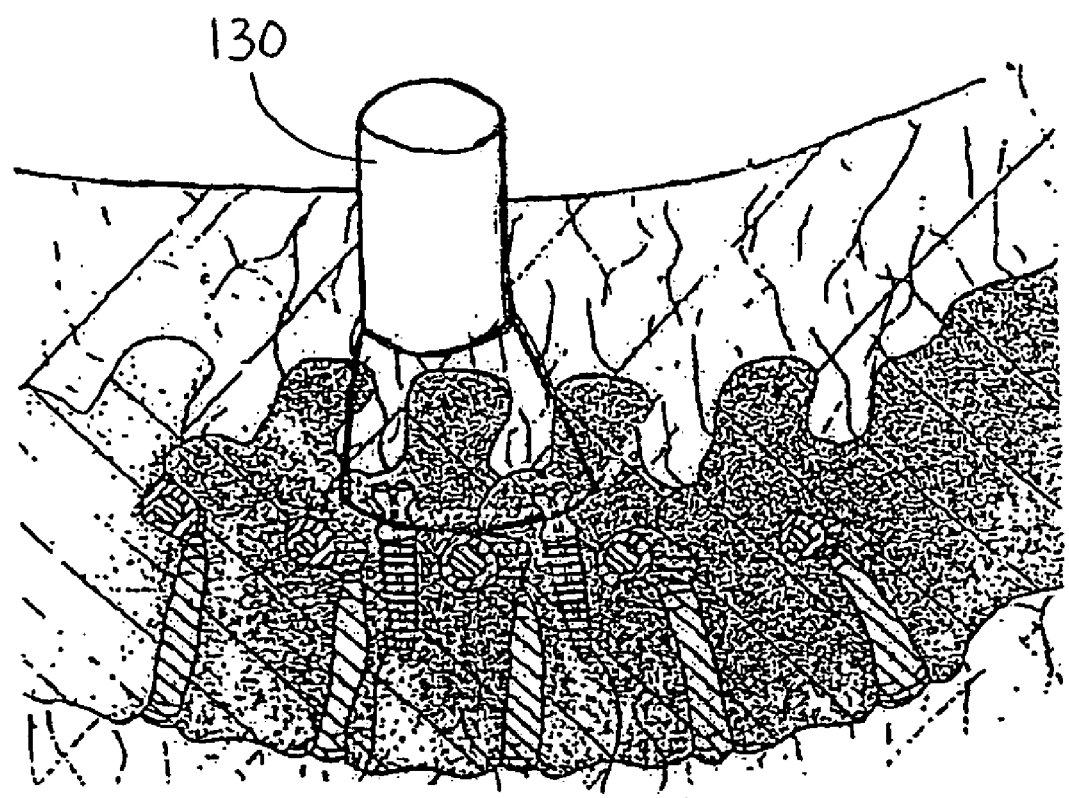
FIG. 35 is a perspective, cross-sectional view of a patient's spine after two pedicle screws have been implanted into designated locations of two adjacent spinal pedicles, in accordance with one embodiment of the invention.

FIG. 35 provides a perspective, cross sectional view of the patient's spinal column after two pedicle screws 2 have been implanted in two respective adjacent pedicles of the spine, in accordance with the present invention. After the pedicle screws 2 are in place, a flexible rod, plate or hybrid connection unit as described above with respect to FIGS. 4-20 may be connected to the pedicle screws to provide flexible stabilization of the spine. Thereafter, the retractor 130 is removed and the minimally invasive incision is closed and/or stitched.

Figure 36A:
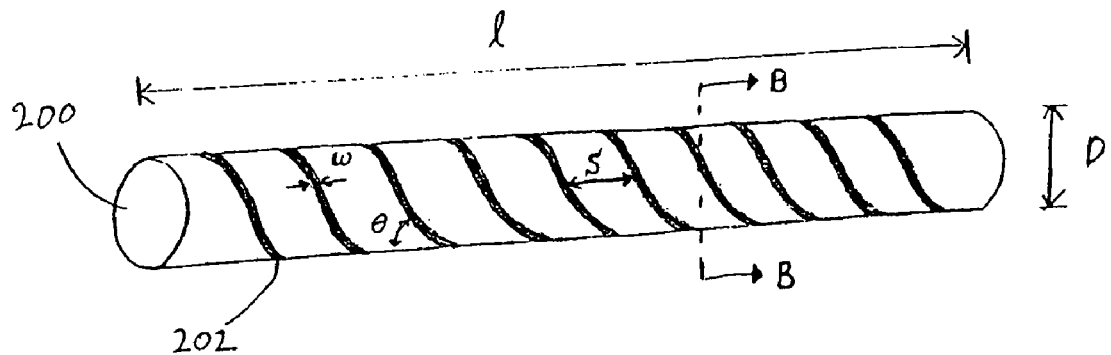
FIG. 36A is perspective view of a flexible rod for spinal fixation having a spiral groove cut therein, in accordance with one embodiment of the present invention.

FIG. 36A illustrates a perspective view of a flexible rod 200 for spinal fixation, in accordance with a further embodiment of the invention. The rod 200 is configured to be secured by securing members 2 as described above with reference to FIGS. 1-3. In preferred embodiments, the rod 200, and rods 210, 220, 230 and 240 described below, are comprised of a solid cylindrically-shaped rod made of known bio-compatible materials such as: stainless steel, iron steel, titanium, titanium alloy, NITINOL, and other suitable metal compositions or materials. As shown in FIG. 36A, spiral grooves 202 are cut or formed along at least a portion of the length of the cylindrical body of the rod 200. In an exemplary embodiment, the length of the rod "l" may be between 4 and 8 centimeters (cm), and its cylindrical diameter "D" is between 4-8 millimeters (mm). The spiral grooves 202 have a width "w" between 0.1 and 0.5 mm and a spiral angle $\theta$ between 50 and 85 degrees from horizontal. The distance between spiral grooves 202 can be between 3 and 6 mm. However, as understood by those skilled in the art, the above dimensions are exemplary only and may be varied to achieve desired flexibility, torsion and strength characteristics that are suitable for a particular patient or application.

Figure 36B:
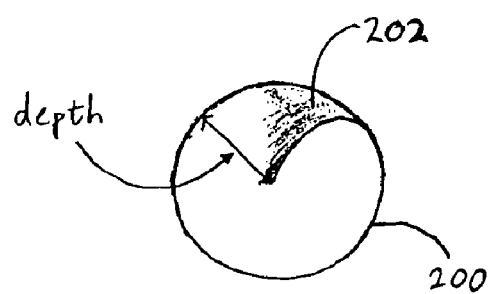
FIG. 36B provides a cross-sectional view of the flexible rod of FIG. 36A, taken along lines B-B of FIG. 36A.

FIG. 36B illustrates a cross-sectional view of the flexible rod 200, taken along lines B-B of FIG. 36A. As shown, spiral groove 202 is cut toward the center longitudinal axis of the cylindrical rod 200. In one embodiment, the depth of the groove 202 is approximately equal to the cylindrical radius of the rod 200, as shown in FIG. 36B, and penetrates as deep as the center longitudinal axis of the cylindrical rod 200. However, the depth and width of the groove 202 can be varied to adjust the mechanical and structural characteristics of the rod 200 as desired.

Figure 37A:
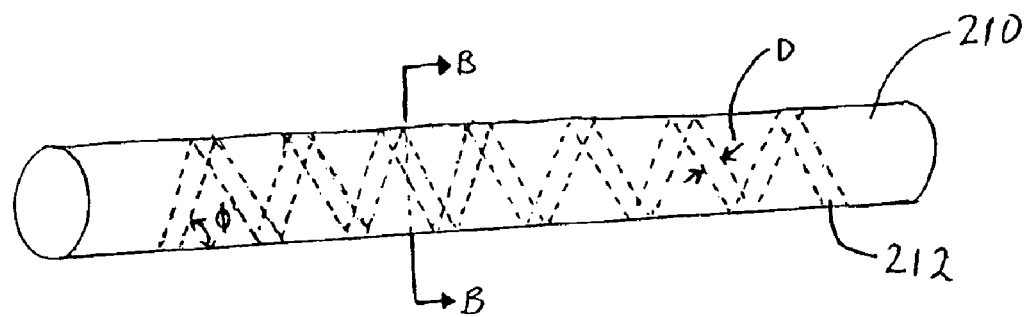
FIG. 37A illustrates a perspective view of a flexible rod for spinal fixation having transverse tunnels within the body of the rod, in accordance with one embodiment of the invention.

FIG. 37A illustrates a flexible rod 210 for spinal fixation in accordance with another embodiment of the invention. The rod 210 includes a plurality of transverse holes or tunnels 212 drilled or formed within the body of the rod 210. In one embodiment, the tunnels 212 pass through a center longitudinal axis of the cylindrical rod 210 at an angle $\Phi$ from horizontal. The openings for each respective tunnel 212 are located on opposite sides of the cylindrical wall of the rod 210 and adjacent tunnels 212 share a common opening on one side of the cylindrical wall, forming a zig-zag pattern of interior tunnels 212 passing transversely through the central longitudinal axis of the rod 210, as shown in FIG. 37A. In one embodiment, the diameter D of each tunnel 212 may be varied between 0.2 to 3 mm, depending the desired mechanical and structural characteristics (e.g., flexibility, torsion and strength) of the rod 210. However, it is understood that these dimensions are exemplary and other diameters D may be desired depending on the materials used and the desired structural and mechanical characteristics. Similarly, the angle from horizontal $\Phi$ may be varied to change the number of tunnels 212 or the distance between adjacent tunnels 212.

Figure 37B:
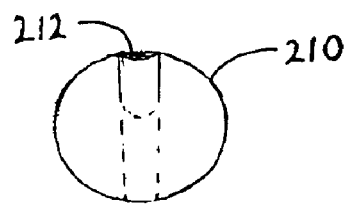
FIG. 37B is a cross-sectional view of the flexible rod of FIG. 37A, taken along lines B-B of FIG. 37A.

FIG. 37B illustrates a cross-sectional view of the flexible rod 210 taken along lines B-B of FIG. 37A. The tunnel 212 cuts through the center cylindrical axis of the rod 210 such that openings of the tunnel 212 are formed at opposite sides of the cylindrical wall of the rod 210.

Figure 38A:
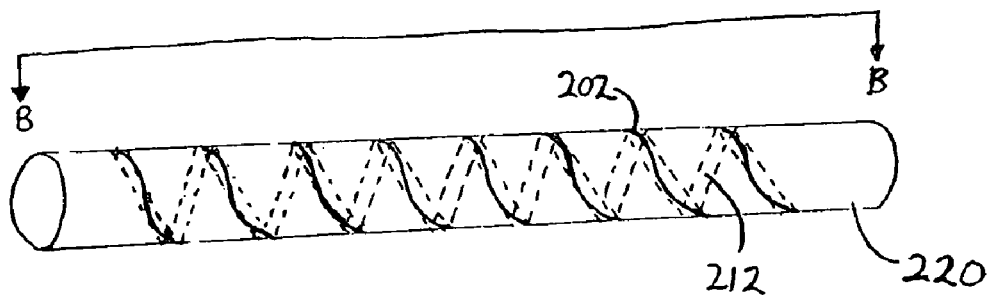
FIG. 38A is a perspective view of a flexible rod for spinal fixation having a spiral groove cut therein and transverse tunnels in the body of the rod, in accordance with a further embodiment of the invention.

FIG. 38A illustrates a perspective view of a flexible rod 220 for spinal fixation, in accordance with a further embodiment of the invention. Rod 220 incorporates the spiral grooves 202 described above with reference to FIGS. 36A and 36B as well as the transverse tunnels 212 described above with respect to FIGS. 37A and 37B. The spiral grooves 202 are cut into the surface of the cylindrical wall of the rod 220 toward a center longitudinal axis of the rod 220. As discussed above, the dimensions of the spiral grooves 202 and their angle from horizontal $\theta$ (FIG. 36A) may be varied in accordance with desired mechanical and structural characteristics. Similarly, the dimensions of the transverse tunnels 212 and their angle from horizontal $\Phi$ (FIG. 37A) may be varied in accordance with desired mechanical and structural characteristics. In one embodiment, the angles $\theta$ and $\Phi$ are substantially similar such that the openings of the tunnels 212 substantially coincide with the spiral grooves 202 on opposite sides of the cylindrical wall of the rod 220.

FIG. 38B shows a top view of the flexible rod 220 taken along the perspective indicated by lines B-B of FIG. 38A. As shown in FIG. 38B, the openings of the tunnels 212 coincide with the spiral grooves 202. By providing both spiral grooves 202 and transverse tunnels 212 within a solid rod 220, many desired mechanical and structural characteristics that are suitable for different patients, applications and levels of spinal fixation may be achieved.

FIG. 39A illustrates a flexible rod 230 for spinal fixation, in accordance with another embodiment of the invention. The rod 230 includes a plurality of transverse tunnels 232 formed in the body of the rod 230. The tunnels 232 are substantially similar to the tunnels 212 described above with respect to FIGS. 37A and 37B, however, the tunnels 232 are not linked together in a zig-zag pattern. Rather, each tunnel 232 is substantially parallel to its immediate adjacent tunnels 232 and the openings of one tunnel 232 do not coincide with the openings of adjacent tunnels 232. As shown in FIG. 39A, the angle from horizontal $\Phi$ in this embodiment is approximately 90 degrees. However, it is understood that other angles Φ may be incorporated in accordance with the present invention. It is further understood that the dimensions, size and shape of the tunnels 232 (as well as tunnels 212) may be varied to achieve desired mechanical and structural characteristics. For example, the cross-sectional shape of the tunnels 212 and 232 need not be circular. Instead, for example, they may be an oval or diamond shape, or other desired shape.

FIG. 39B illustrates a cross-sectional view of the rod 230 taken along lines B-B of FIG. 39A. As shown in FIG. 39B, the transverse tunnel 232 travels vertically and transversely through the center longitudinal axis of the rod 230. FIG. 39C illustrates a cross-sectional view of a further embodiment of the rod 230, wherein an additional transverse tunnel 232' is formed substantially orthogonal to the first transverse tunnel 232 and intersect the first transverse tunnel 232 at the center, cylindrical axis point. In this way, further flexibility of the rod 230 may be provided as desired.

Figure 40A:
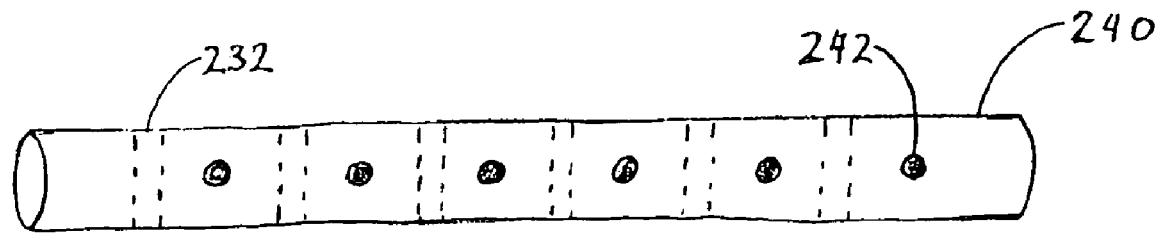
FIG. 40A illustrates a perspective view of a flexible rod for spinal fixation, in accordance with a further embodiment of the invention.
Figure 40B:
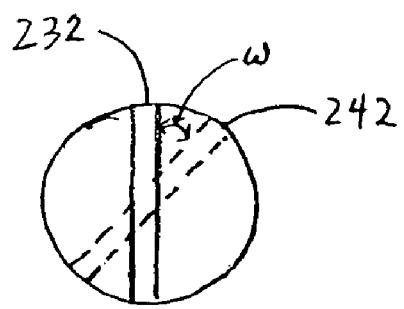
FIG. 40B illustrates a cross-sectional view of a flexible rod for spinal fixation in accordance with a further embodiment of the invention.

FIG. 40A illustrates a perspective view of a flexible rod 240, in accordance with a further embodiment of the invention. The rod 240 includes a plurality of interleaved transverse tunnels 232 and 242 which are substantially orthogonal to each other and which do not intersect, as shown in FIG. 40A. In another embodiment, a cross-sectional view of which is shown in FIG. 40B, adjacent tunnels 232 and 242 need not be orthogonal to one another. Each tunnel 232, 242 can be offset at a desired angle ω from its immediately preceding adjacent tunnel 232, 242. As can be verified by those of skill in the art, without undue experimentation, by varying the dimensions of the tunnels, their numbers, and their angular directions with respect to one another, various desired mechanical and structural characteristics for flexible rods used in spinal fixation devices may be achieved.

Various embodiments of the invention have been described above. However, those of ordinary skill in the art will appreciate that the above descriptions of the preferred embodiments are exemplary only and that the invention may be practiced with modifications or variations of the devices and techniques disclosed above. Those of ordinary skill in the art will know, or be able to ascertain using no more than routine experimentation, many equivalents to the specific embodiments of the invention described herein. Such modifications, variations and equivalents are contemplated to be within the spirit and scope of the present invention as set forth in the claims below.

What is claimed is:

1. A flexible rod system for use in a spinal fixation device comprising:
   a first pedicle screw and a second pedicle screw;
   a flexible rod mounted between the first pedicle screw and the second pedicle screw such that the flexible rod limits movement of a first vertebra relative to a second vertebra, the flexible rod comprising:
   a first end;
   a second end; and
   a longitudinal substantially cylindrical center section having a longitudinal axis and an outer surface, the center section being located between and coupled to the first end and the second end, the center section including a plurality of grooves formed in the outer surface of the substantially cylindrical center section, the plurality of grooves extending circumferentially around the longitudinal axis and a plurality of holes formed in the substantially cylindrical center section, each hole intersecting an end of at least two of the plurality of grooves formed in the outer surface of the rod.

2. The flexible rod of claim 1, wherein the rod is made from a material selected from the group consisting of: stainless steel, iron steel, titanium, titanium alloy and NITINOL.

3. The flexible rod of claim 1, wherein the grooves are cut toward a center longitudinal axis of the rod and each one of the plurality of grooves is associated with a first hole at a first end and a second hole at a second end.

4. The flexible rod of claim 1, wherein the rod is solid along a longitudinal section.

5. The flexible rod of claim 4, further including a plurality of transverse tunnels formed within at least a portion of the solid longitudinal section and wherein each tunnel coincided with at least one hole.

6. The flexible rod of claim 5, wherein the rod is solid and the first end, the second end, and the center section are monolith and each transverse tunnel passes through a center longitudinal axis of the cylindrical portion of the rod such that openings for each respective transverse tunnel are located on opposite sides of the rod and coincides with at least one of the holes.

7. The flexible rod of claim 1, wherein the first end, the second end, and the center section are a monolith.

8. The flexible rod of claim 5, wherein each of said plurality of transverse tunnels have an internal diameter between 0.2 and 3 millimeters.

9. A connection unit for use in bony fixation, comprising:
   a first bone coupling assembly including a first bone anchor; and
   a longitudinal solid metal rod having an outer surface, including:
   a first end received by and coupled to the first bone coupling assembly;
   a second end; and
   a substantially cylindrical center section located between and coupled to the first end and the second end, the center section including a plurality of grooves formed in the outer surface of the rod, and a plurality of tunnels formed in the center section of the rod, each tunnel including a pair of diametrically opposed openings on the outer surface of the rod, wherein the tunnel openings intersect one of the grooves formed in the outer surface of the rod.

10. The connection unit of claim 9, wherein the rod is made from a material selected from the group consisting of: stainless steel, iron steel, titanium, titanium alloy and NITINOL.

11. The connection unit of claim 9, wherein the grooves are cut toward a center longitudinal axis of the rod.

12. The connection unit of claim 9, wherein the first end, the second end, and the center section are a monolith.

13. The connection unit of claim 9, wherein each of said plurality of tunnels have an internal diameter between 0.2 and 3 millimeters.

14. The connection unit of claim 9, wherein the tunnels pass through a center longitudinal axis of the cylindrical center section of the rod.

15. The connection unit of claim 9, wherein adjacent tunnels share a common opening on one side of the outer surface of the rod thus forming a zig-zag pattern of tunnels passing transversely through a central longitudinal axis of the rod.

16. The connection unit of claim 9, wherein the tunnel has a diameter and the grooves have a width, the diameter of the tunnel is at least twice as wide as the width of the grooves.

17. The connection unit of claim 9, wherein each tunnel has a longitudinal axis, the longitudinal axis of each tunnel being substantially parallel to the longitudinal axis of an adjacent tunnel so that the tunnels are substantially parallel with respect to one another.

18. The connection unit of claim 9, wherein each tunnel has a longitudinal axis, each tunnel is substantially orthogonal to an adjacent tunnel.

19. The connection unit of claim 18, wherein each tunnel intersects at least one adjacent tunnel.

20. A connection unit for use in a spinal fixation device comprising:
- a first bone coupling assembly including a first bone anchor;
- a second bone coupling assembly including a second bone anchor; and
- a flexible rod including:
  - a first end received by and coupled to the first bone coupling assembly;
  - a second end received by and coupled to the second bone coupling assembly, the first and second bone coupling assemblies capable of securing the rod between a first vertebra and a second vertebra such that the flexible rod limits movement of the first vertebra relative to the second vertebra; and
  - a longitudinal substantially cylindrical center section having a longitudinal axis and an outer surface, the center section being located between and coupled to the first end and the second end, the center section including a plurality of grooves formed in the outer surface of the substantially cylindrical center section, the plurality of grooves extending circumferentially around the longitudinal axis and a plurality of holes formed in the substantially cylindrical center section, each hole intersecting an end of at least two of the plurality of grooves formed in the outer surface of the rod.

* * * * *